US012727995B2

(12) United States Patent
Peckels et al.

(10) Patent No.: US 12,727,995 B2
(45) Date of Patent: Sep. 8, 2026

(54) TRANSCATHETER PROSTHETIC ATRIOVENTRICULAR VALVE WITH HINGED STENT

(71) Applicant: St. Jude Medical, Cardiology Division, Inc., St. Paul, MN (US)

(72) Inventors: William H. Peckels, Robbinsdale, MN (US); Randolf Von Oepen, Aptos, CA (US); Heath Marnach, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 441 days.

(21) Appl. No.: 18/504,696

(22) Filed: Nov. 8, 2023

(65) Prior Publication Data

US 2024/0164894 A1 May 23, 2024

Related U.S. Application Data

(60) Provisional application No. 63/384,835, filed on Nov. 23, 2022.

(51) Int. Cl.
*A61F 2/24* (2006.01)

(52) U.S. Cl.
CPC .... *A61F 2/2418* (2013.01); *A61F 2220/0075* (2013.01); *A61F 2250/0069* (2013.01)

(58) Field of Classification Search
CPC ............ A61F 2/2418; A61F 2002/9155; A61F 2/915; A61F 2002/91525; A61F 2230/0045; A61F 2250/0018; A61F 2250/0073
See application file for complete search history.

(56) References Cited

U.S. PATENT DOCUMENTS 8,920,488 B2 * 12/2014 Bregulla .................. A61F 2/91 623/1.16
9,901,447 B2 2/2018 Braido
2003/0149477 A1 8/2003 Gabbay
2008/0215135 A1 * 9/2008 Seguin ..................... A61F 2/91 623/1.35
2009/0163996 A1 6/2009 Bregulla
2010/0256723 A1 * 10/2010 Murray ................ A61F 2/2418 623/1.2

(Continued)

FOREIGN PATENT DOCUMENTS

WO 2010141847 A1 12/2010

*Primary Examiner* — Javier G Blanco
(74) *Attorney, Agent, or Firm* — SLEMAN & LUND LLP

(57) ABSTRACT

A prosthetic heart valve for replacing a native atrioventricular valve includes a collapsible and expandable frame having atrial and ventricular portions each including a circumferential row of cells, and a center portion extending between the atrial and ventricular portion. The atrial portion and the ventricular portion may flare radially outwardly from the center portion in an expanded condition of the frame. A plurality of prosthetic leaflets may be mounted to the frame. At least some of the struts forming the cells in the atrial portion include an undulating structure positioned between two axially extending strut portions, the undulating structure including at least one circumferentially extending strut portion and being configured to dampen forces transmitted across the undulating structure between the two axially extending strut portions.

18 Claims, 18 Drawing Sheets

(56) References Cited

U.S. PATENT DOCUMENTS

| | | | | |
|---|---|---|---|---|
| 2010/0292777 | A1* | 11/2010 | Meyer | A61F 2/915 623/1.16 |
| 2016/0354204 | A1* | 12/2016 | Braido | A61F 2/915 |
| 2018/0000580 | A1* | 1/2018 | Wallace | A61F 2/2409 |
| 2018/0125650 | A1 | 5/2018 | Nasr | |

* cited by examiner

TRANSCATHETER PROSTHETIC ATRIOVENTRICULAR VALVE WITH HINGED STENT

CROSS-REFERENCE TO RELATED APPLICATIONS

This application claims priority to and benefit of the filing date of U.S. Provisional Patent Application No. 63/384,835, filed Nov. 23, 2022, the disclosure of which is hereby incorporated by reference herein.

BACKGROUND OF THE DISCLOSURE

Heart valve disease is a significant cause of morbidity and mortality. One treatment for this disease is valve replacement. One form of replacement device is a bioprosthetic valve. Collapsing these valves to a smaller size or into a delivery system enables less invasive delivery approaches compared to conventional open-chest, open-heart surgery. Collapsing the implant to a smaller size and using a smaller delivery system minimizes the access site size and reduces the number of potential periprocedural complications.

The size to which an implant can be collapsed is limited by the volume of materials used in the implant, the strengths and shapes of those materials, and the need to function after expansion (or re-expansion). Using multiple steps and/or multiple delivery system devices may increase the time and complexity of a procedure.

Native atrioventricular valves (i.e., the tricuspid valve and the mitral valve) typically have a larger size and/or diameter compared to the native aortic valve and the native pulmonary valve. Among the native atrioventricular valves, a regurgitant tricuspid valve typically has a larger size and/or diameter than a regurgitant mitral valve. For example, for patients with severe tricuspid valve regurgitation, the diameter of the tricuspid valve may range from about 40 mm to about 66 mm, although these numbers are merely exemplary. As a result, prosthetic heart valve designs and considerations for replacing the different native heart valves are not identical. For example, to accommodate the large size of the mitral and tricuspid valve, recent prosthetic heart valve designs have included an outer frame with a large size to engage the native mitral or tricuspid annulus, and a smaller and generally cylindrical inner frame within that outer frame, the inner frame housing the prosthetic valve leaflets. However, this double-stented design generally increases the bulk of the prosthetic heart valve, resulting in a larger profile when collapsed within a delivery device. This, in turn, requires the delivery device (e.g., a catheter housing the collapsed prosthetic heart valve for delivery) to have a larger size to accommodate the large prosthetic heart valve. Typically, it is desirable for catheters of transcatheter heart valve delivery devices to have a smaller size, since the catheters may need to pass through the vasculature to reach the native heart valve in a minimally invasive manner. Thus, it would be desirable to have a prosthetic heart valve that is able to fit within a native tricuspid or mitral valve but is able to collapse to a small size to be accommodated in a relatively small profile delivery device.

BRIEF SUMMARY OF THE DISCLOSURE

According to one aspect of the disclosure, a prosthetic heart valve for replacing a native atrioventricular valve includes a collapsible and expandable frame. The frame may include an atrial portion including a circumferential row of cells, a ventricular portion including a circumferential row of cells, and a center portion extending between the atrial portion and the ventricular portion. The atrial portion and the ventricular portion may flare radially outwardly from the center portion in an expanded condition of the frame. A plurality of prosthetic leaflets may be mounted to the frame. At least some of the struts forming the cells in the atrial portion include an undulating structure positioned between two axially extending strut portions, the undulating structure including at least one circumferentially extending strut portion and being configured to dampen forces transmitted across the undulating structure between the two axially extending strut portions. The frame may include a number of undulating structures so that force applied to an inflow-most tip of any atrial cell in the atrial portion cannot transmit to an outflow-most tip of any ventricular cell without passing through at least one of the undulating structures. Each of the atrial cells may intersect with a circumferentially adjacent atrial cell at a strut junction, and each of the strut junctions may include the undulating structure. Each undulating structure may include a first curved portion extending from a first one of the two axially extending strut portions, and a second curved portion extending from a second one of the two axially extending strut portions. The at least one circumferentially extending strut portion may couple the first curved portion to the second curved portion. The first curved portion may extend in a first circumferential direction, and the second curved portion may extend in a second circumferential direction opposite the first circumferential direction.

The two axially extending strut portions may include a first inflow-side axially extending strut portion and a second outflow-side axially extending strut portion. The first inflow-side axially extending strut portion may include a first eyelet formed therein, and the second outflow-side axially extending strut portion may include a second eyelet formed therein. A suture member may pass into the first eyelet and the second eyelet so that the suture member couples the first inflow-side axially extending strut portion to the second outflow-side axially extending strut portion. The suture member may be configured to prevent the undulating portion from straightening upon application of a tensile force. The suture member may be configured to allow the undulating portion to compress upon application of a compressive force. Each circumferentially extending strut portion may have a length that is greater than a distance between circumferentially adjacent pairs of the first inflow-side axially extending strut portions. Each circumferentially extending strut portion may be offset, in an axial direction, from circumferentially adjacent pairs of circumferentially extending strut portions. Each of the first inflow-side axially extending strut portions may have an axial length that is different from the axial length of circumferentially adjacent pairs of the first inflow-side axially extending strut portions. A sealing skirt may be positioned on an exterior surface of the frame. The frame may include a plurality of commissure attachment features ("CAFs"), each of the prosthetic leaflets being coupled to the frame via the CAFs. Each CAF may be an axially extending beam including a single column of eyelets. Each CAF may include a pair of circumferentially adjacent eyelets adjacent to each end of the single column of eyelets. Each CAF may be coupled to struts that extend to the center portion of the frame, so that in the expanded condition of the frame, the CAFs are generally axially aligned with the center portion of the frame and the center portion of the frame defines a minimum diameter of the frame. The frame may include a plurality of tines on the ventricular portion, each of the plurality of tines extending to a free end pointing toward the atrial portion in a collapsed condition of the frame.

DETAILED DESCRIPTION OF THE DISCLOSURE

Figure 1:
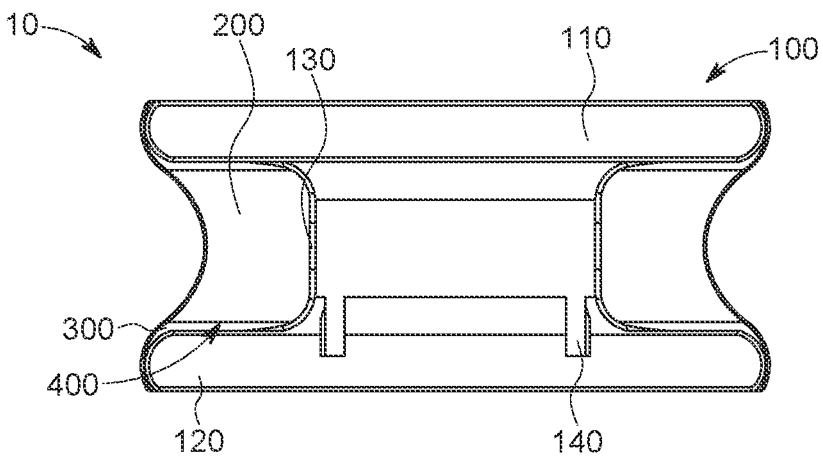
FIG. 1 is a cross-section of a prosthetic heart valve, taken along section line 1-1 of FIG. 2.

As used herein, the term inflow, when used in connection with a prosthetic heart valve, refers to the end of the prosthetic heart valve through which blood first flows when flowing in the antegrade direction, and the term outflow refers to the end of the prosthetic heart valve through which blood last flows when flowing in the antegrade direction. Further, although the disclosure focuses on prosthetic tricuspid valve replacements, the disclosure may apply with similar force to prosthetic mitral valve replacements. Thus, unless otherwise expressly specified, the embodiments described herein may be used for replacing either a native tricuspid valve or a native mitral valve (with or without additional modifications specific to the heart valve being replaced), even if a particular embodiment may be more suited for replacing either the native tricuspid valve or the native mitral valve.

As explained in the background of the disclosure, prosthetic heart valves that include an anchoring frame and a valve frame nested within the anchoring frame typically have larger sizes (e.g. larger crimped diameters) when collapsed within a delivery device. As an example, this type of prosthetic heart valve may only fit within a delivery device that has a catheter with an inner diameter that is 30-33 French (10-11 mm in diameter) or larger. For transcatheter prosthetic mitral or tricuspid valves that are delivered intravascularly through the femoral vein, a delivery catheter having an outer diameter of 30-33 French or larger may increase the likelihood of access site complications, which may require a surgeon to intervene, as well as requiring a surgical cut down to gain access to the vasculature and a follow-up surgical repair after the procedure is complete. The prosthetic heart valves disclosed herein have features and configurations that are intended to allow for the prosthetic heart valves to reliably anchor within the larger size annulus of the tricuspid valve (or the mitral valve) while being able to collapse into a delivery catheter having an inner diameter of 30-33 French or smaller. It should be understood that, as used herein, the unit French refers to the inner diameter of a catheter when describing the ability of a valve to fit within that catheter, whereas the unit French refers to the outer diameter of the catheter when describing how catheter size may result in vascular access problems.

As is described below, one way to achieve this functionality is to design the prosthetic heart valve with a single support stent (e.g., a single stent layer or a non-nested frame configuration) that can span the large atrioventricular valve annulus diameters found in patients who experience heart failure. The geometry of the support stent may allow for prosthetic leaflets to be secured inside, with atrial and/or ventricular flanges or disks that have a large enough diameter or profile to sandwich, clamp, and/or overlie the native annulus tissue therebetween. To provide adequate sealing between the support stent and the native valve annulus, fabric(s) may span the gap between the atrial and ventricular disks, where the fabric(s) are capable of elongating to mitigate the effects of foreshortening when sheathing the prosthetic heart valve into the catheter. While the embodiments described below may be suitable for replacing either a tricuspid or mitral valve, these embodiments may be best suited for replacing a tricuspid valve due to the lower right ventricular pressures compared to left ventricular pressures, which may reduce the need for a nested stent design. It should be understood that, although the terms “frame” and “stent” are generally used interchangeably herein, the term “stent” does not imply any special structure or function beyond being a frame.

Figure 2:
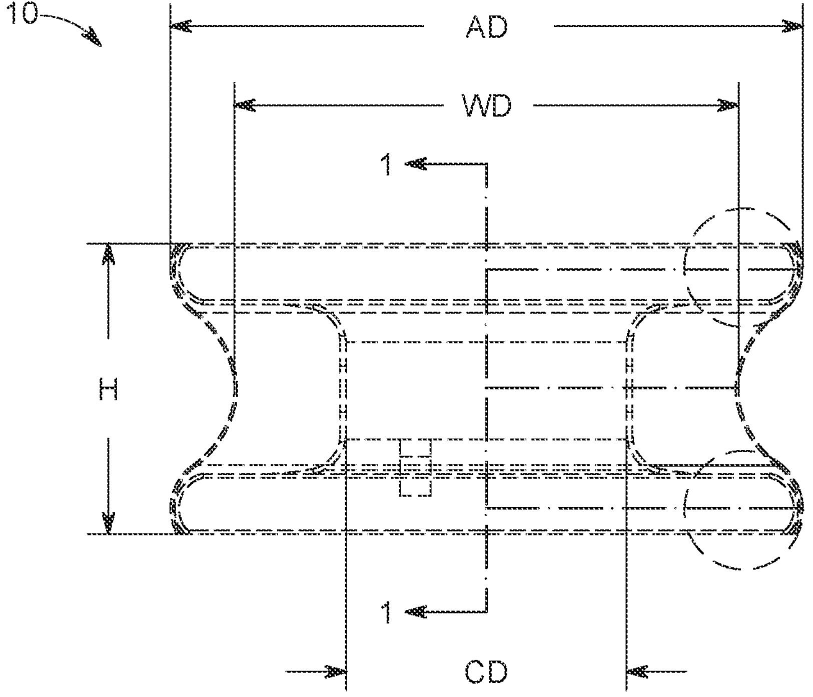
FIG. 2 is a schematic side view of the prosthetic heart valve of FIG. 1.
Figure 4:
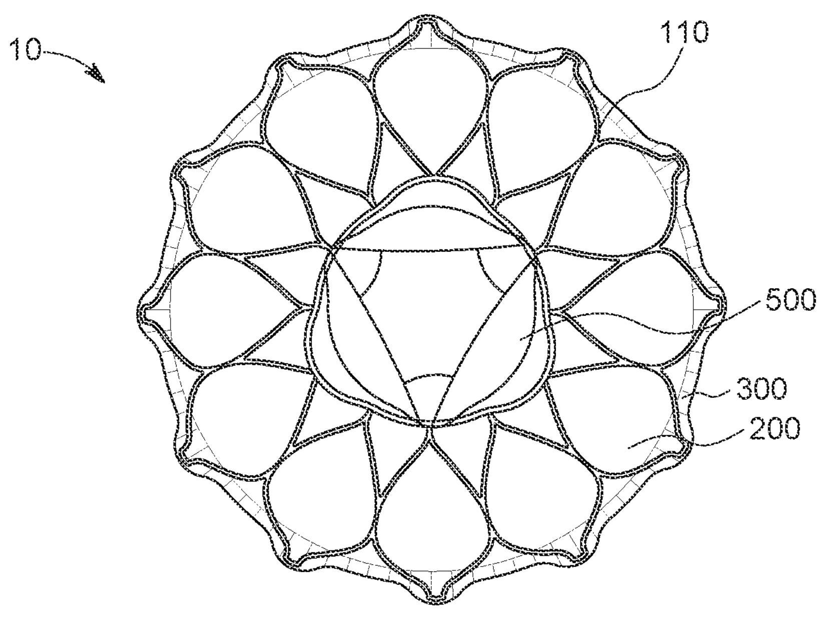
FIG. 4 is a top or atrial view of the prosthetic heart valve of FIGS. 1-2.
Figure 5:
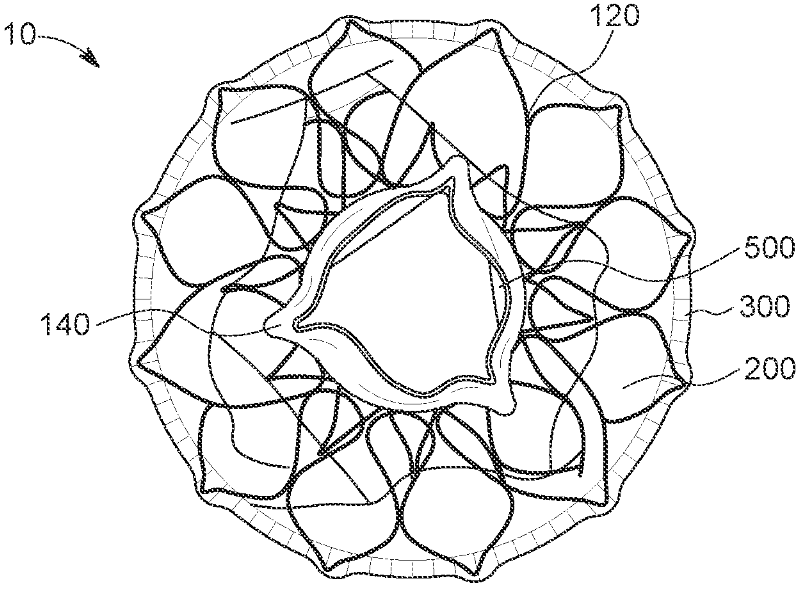
FIG. 5 is a bottom or ventricular view of the prosthetic heart valve of FIGS. 1-2.

FIG. 1 is a cross-section of a prosthetic heart valve 10, taken along section line 1-1 of FIG. 2, according to one aspect of the disclosure. Generally, prosthetic heart valve 10 includes a support frame or stent 100, which may include an atrial flange 110 (which may alternately be referred to as an atrial disk or anchor), a ventricular flange 120 (which may alternately be referred to as a ventricular disk or anchor), and a central stent portion 130 (which may be referred to as a central waist). The stent 100 may also include a plurality of commissure attachment features (“CAFs”) 140 for use in coupling the prosthetic valve leaflets 500 to the stent 100. The prosthetic valve leaflets 500 are omitted from the illustration of FIGS. 1-2 and are best shown in FIGS. 4-5. The stent 100 is described in greater detail below in connection with FIGS. 6-7. Referring still to FIG. 1, the prosthetic heart valve 10 may include a first fabric 200 generally surrounding the central portion 130 of the stent 100 and spanning the gap between the atrial disk 110 and the ventricular disk 120. In one embodiment, the first fabric may be formed as a knitted fabric (e.g., polyethylene terephthalate ("PET"), polytetrafluoroethylene ("PTFE"), ultra-high molecular weight polyethylene ("UHMWPE"), polyester, or similar materials). The formation of the first fabric 200 as a knitted fabric may allow for significant stretching of the first fabric, e.g., up to doubling or tripling in length upon being stretched. In one embodiment, the first fabric 200 is configured to stretch to increase its length by a factor of about 2.5. When in the expanded or deployed condition shown in FIG. 1, a substantial amount of open space or volume may exist between the first fabric 200 and the outside of the stent 100, at least prior to implantation. A second fabric 300 may be provided on the outer surface of the atrial disk 110 and the ventricular disk 120, the second fabric 300 being coupled to the first fabric 200 at seams 400, which may be for example ultrasonic welding seams. In one embodiment, the second fabric 300 may be formed as a woven fabric (e.g., PET, PTFE, UHMWPE, etc.). By forming the second fabric 300 as a woven fabric, the second fabric 300 may be particularly suited to provide sealing functionality against the native anatomy, while the knitted fabric 200 is particularly suited to provide stretching capabilities to allow for relatively unhindered collapsing and expanding of the stent 100. Even if the first fabric 200 is formed as a knit fabric and the second fabric 300 is formed as a woven fabric, it may be desirable (although not required) for the two fabrics to be formed of the same material, with the stretch and/or sealing properties being influenced, at least in part, by the way in which the threads of the fabric are wound, knitted, and/or woven. For example, changing the bias of the warp versus the weft will change the stretch capabilities of a fabric.

Referring briefly to FIG. 2, various exemplary dimensions of the prosthetic heart valve 10 when the prosthetic heart valve 10 is in an expanded or deployed configuration are provided. However, these dimensions are merely exemplary and other dimensions may be suitable. For example, the outer anchor diameter AD of the atrial disk 110 and/or ventricular disk 120 may be about 65 mm. However, in other embodiments, the anchor diameter AD may be between about 50 mm and about 80 mm. In the expanded or deployed condition (e.g., upon implantation into the native tricuspid valve annulus), the first fabric 200 may form a waisted shape with a minimum waist diameter WD near an axial center of the first fabric 200. In the illustrated embodiment, the waist diameter WD may be about 52 mm, but in other embodiments, the waist diameter WD may be between about 45 mm and about 75 mm. The center portion 130 of the stent 100 may be generally cylindrical, and in the illustrated embodiment has a central diameter CD of about 29 mm, but in other embodiments, the central diameter CD may be between about 25 mm and about 35 mm. The prosthetic heart valve 10 may have a height H between the inflow and outflow ends of about 30 mm, but in other embodiments, the height may be between about 25 mm and about 45 mm. As noted above, each of these dimensions is merely illustrative. In some embodiments, in the expanded or deployed condition, the ratio of the outer anchor diameter AD to the central diameter CD is between about 2.5:1 and about 1.5:1, preferably between about 2.5:1 and about 2.0:1, including about 2.25:1. As is explained in greater detail below, this large disparity may allow the atrial disk 110 and ventricular disk 120 to be large enough to provide anchoring, but the central portion 130 to be small enough to house an appropriately sized set of prosthetic valve leaflets 500, while still maintaining a small crimp profile for delivery, e.g. capable of being delivered within, and deployed successfully from, a delivery device catheter having an inner diameter as small as 24 French (8.0 mm) or even as small as 18 French (6.0 mm). In some embodiments, the prosthetic heart valve 10 may be successfully housed within a catheter having an inner diameter of between 22 French (7.33 mm) and 32 French (10.66 mm), including between about 24 French (8.0 mm) and 28 French (9.33 mm).

Figure 3:
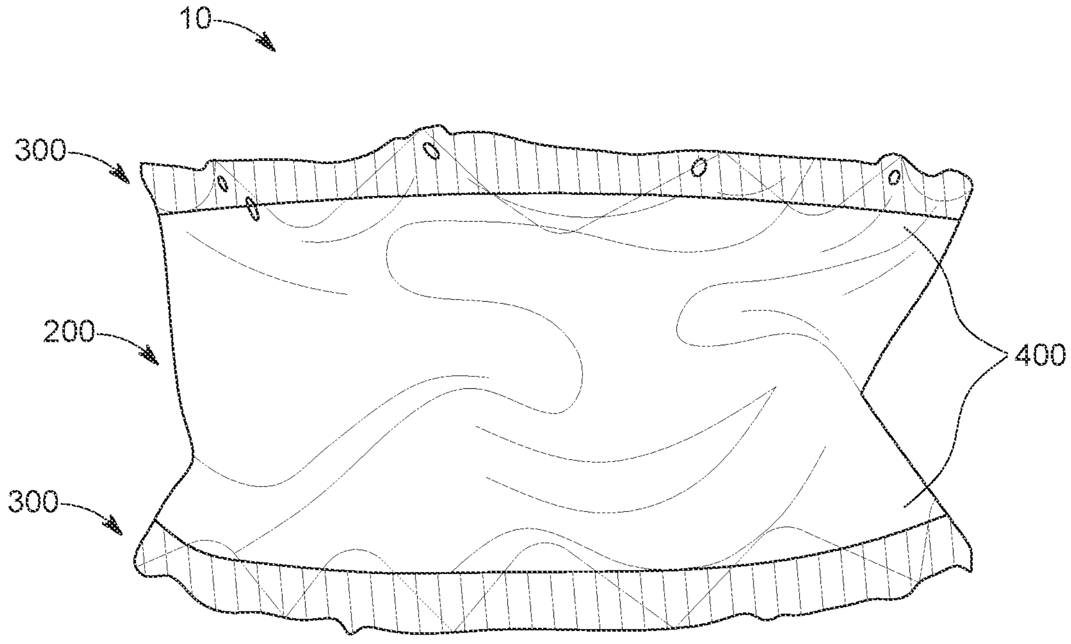
FIG. 3 is a side view of the prosthetic heart valve of FIGS. 1-2.

FIG. 3 is a side view of the prosthetic heart valve 10. FIG. 3 illustrates the prosthetic heart valve 10 in an expanded or deployed condition, with the first fabric 200 extending between the atrial disk 110 and the ventricular disk 120. In the illustrated embodiment, first fabric 200 is a stretchy fabric that can easily elongate when the prosthetic heart valve 10 collapses and foreshorten as the prosthetic heart valve 10 expands. To achieve this elongation and foreshortening, it is preferred that the first fabric 200 is not directly coupled to the stent 100. For example, the fabric 200 preferably is not directly sutured to struts of the stent 100. The second fabric 300 includes a portion coupled to the outside of the atrial disk 110 and a portion coupled to the outside of the ventricular disk 110, for example by suturing. As noted above, the second fabric 300 may function to assist with creating or enhancing the seal between the native valve annulus and the atrial and ventricular portions of the prosthetic heart valve 10. The interfaces 400 between the first fabric 200 and the portions of the second fabric 300 are shown in FIG. 3. In the illustrated example, the interfaces 400 are seams created via ultrasonic welding, but the fabrics may be coupled to each other in any suitable way, including suturing, adhesives, etc. In some embodiments, only a single outer fabric may be used, with the single outer fabric having sufficient stretch capabilities to allow the stent 100 to expand and collapse without significant restriction, but while also providing suitable sealing with the native valve annulus.

FIG. 4 illustrates the prosthetic heart valve 10 in an expanded or deployed condition, as viewed from the atrial or inflow side with the prosthetic leaflets 500 in an open condition. FIG. 5 illustrates the prosthetic heart valve 10 in an expanded or deployed condition, as viewed from the ventricular or outflow side with the prosthetic leaflets 500 in an open condition. In the illustrated embodiment, the prosthetic heart valve 10 includes three prosthetic leaflets 500, but in some embodiments, the prosthetic heart valve 10 may include more or fewer prosthetic leaflets. The prosthetic leaflets 500 may be formed of any suitable material. For example, each prosthetic leaflet 500 may be formed of bioprosthetic tissue, such as porcine or bovine pericardium. In other embodiments, each prosthetic leaflet 500 may be formed of a synthetic material such as a synthetic material or fabric, including PET, UHMWPE, PTFE, etc. Each prosthetic leaflet 500 may have two side portions (e.g., forming leaflet tabs), each side portion being coupled to an end of an adjacent prosthetic leaflet 500 to form a commissure, each leaflet commissure being coupled to a respective CAF 140 of the stent 100. Each leaflet may include an outflow edge between the two side edges, the outflow edge being free to allow for opening and closing of the leaflets during normal operation (e.g., to provide the valve functionality). Each leaflet may include an inflow edge between the two side edges, the inflow edge being coupled (e.g., sutured) to the stent 100. In some embodiments, the inflow edges of the prosthetic leaflets 500 are coupled solely (e.g., via sutures) to struts of the central portion 130 of the stent 100, without any direct attachment to other components. In other embodiments, a short fabric skirt may be provided around a portion of the inflow side of the central portion 130 of the stent 100, with the short fabric skirt coupled to the stent 100 and providing an additional structure that may be used for coupling (e.g., via sutures) the inflow ends of the prosthetic leaflets 500 to the prosthetic heart valve 10.

By comparing FIG. 4 to FIG. 5, it can be seen that the atrial disk 110 is "closed," while the ventricular disk 120 is "open." In other words, as shown in FIG. 4, the inflow ends of the prosthetic leaflets 500 are directly coupled to the stent 100 (and/or a separate short fabric skirt as noted above) so that there is no open flow pathway between the prosthetic leaflets 500 and the outer fabric skirt(s) (e.g., first fabric 200 and second fabric 300, or the single outer fabric if only a single outer fabric is used) at the atrial disk 110. On the other hand, as shown in FIG. 5, the outflow ends of the prosthetic leaflets 500 have a significant radial spacing from the first fabric 200 and the second fabric 300. With this configuration, after implantation of the prosthetic heart valve 10 into the native tricuspid valve, as the right ventricle contracts, the prosthetic leaflets 500 are forced closed and blood tends to flow in the retrograde direction into the space between the prosthetic leaflets 500 and the first fabric 200. The "closed" configuration at the atrial disk 110 ensures that blood cannot actually pass into the right atrium, but the "open" configuration at the ventricular disk 120 allows that retrograde blood to press the first fabric 200 outwardly and into the native valve annulus to enhance the seal between the prosthetic heart valve 10 and the native tricuspid valve annulus.

Figure 6:
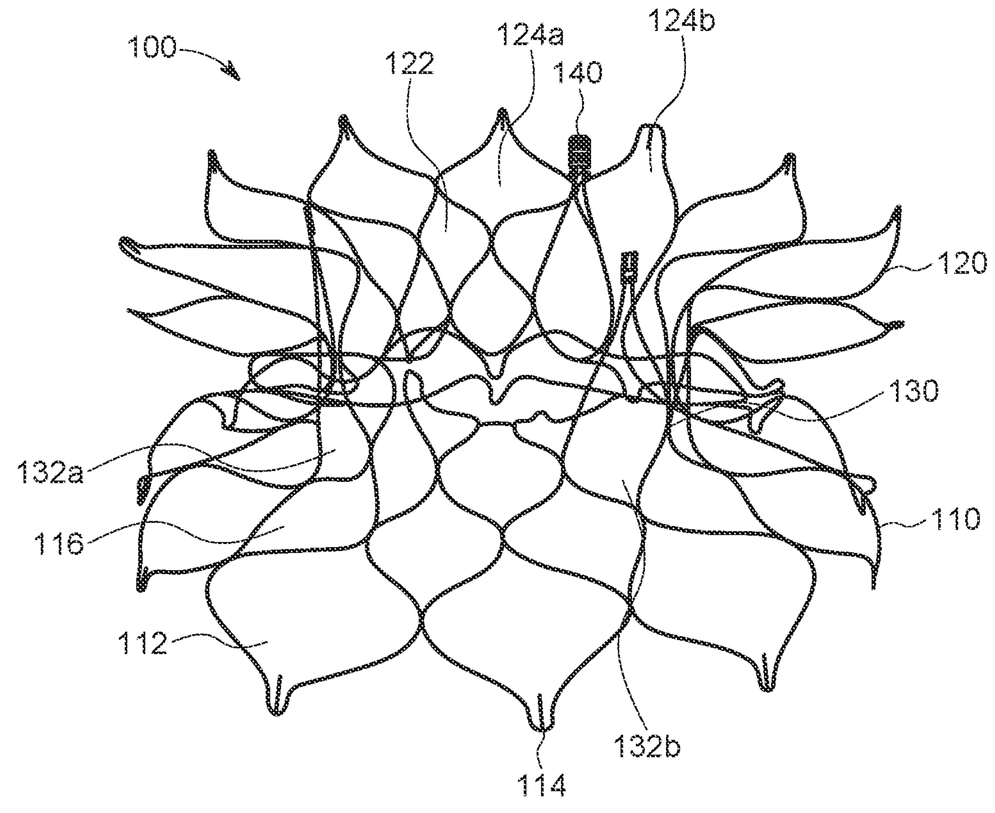
FIG. 6 is a perspective view of the stent of the prosthetic heart valve of FIGS. 1-2 with other components of the prosthetic heart valve omitted.
Figure 7:
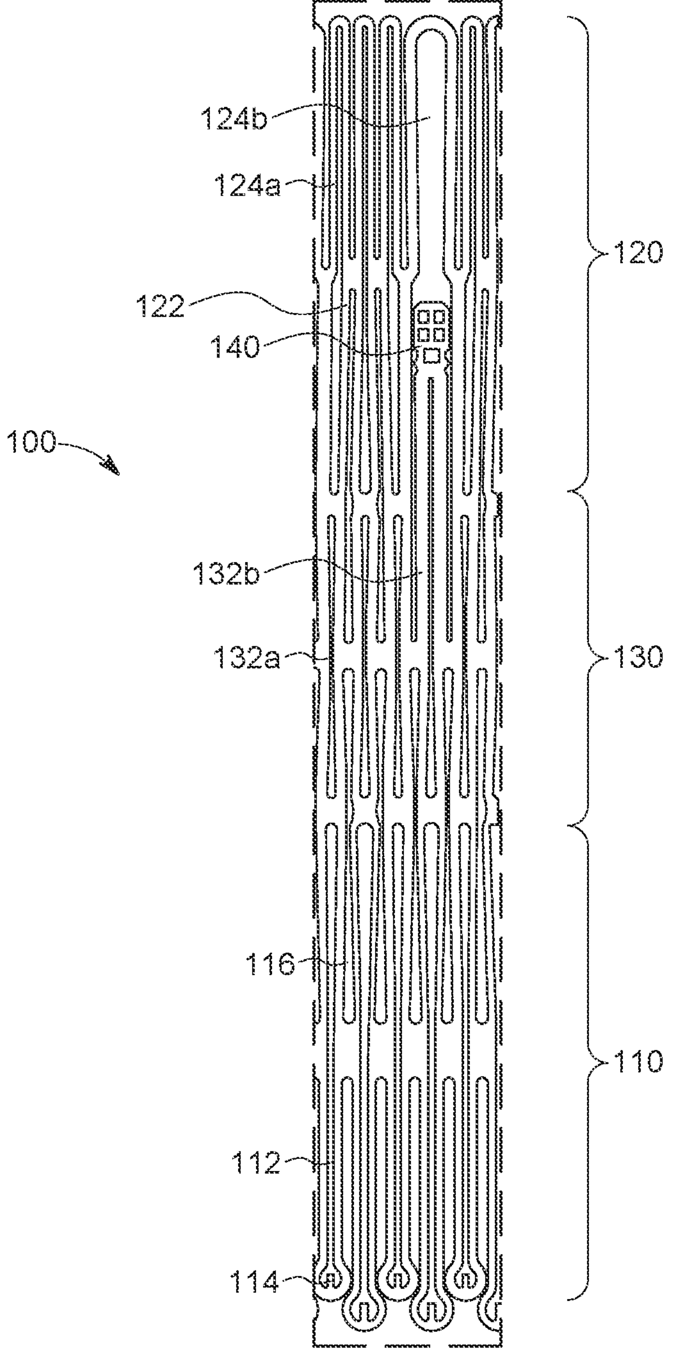
FIG. 7 is a view of a portion of the cut pattern of the stent of FIG. 6.

FIG. 6 is a perspective view of the stent 100 of the prosthetic heart valve 10 in an expanded condition, with other components of the prosthetic heart valve 10 omitted from the figure. The orientation of stent 100 is opposite that shown in FIGS. 1-3. In other words, the top of the view of FIG. 6 is the outflow end and the bottom of the view of FIG. 6 is the inflow end. Stent 100 is preferably formed of a biocompatible shape memory or superelastic material. One particularly suitable example of this stent material is a nickel-titanium alloy, such as Nitinol. However, other materials may be suitable. In one example, stent 100 may be formed by laser cutting a hollow tube of Nitinol, and then shape-setting the stent 100 to the desired shape, for example by heat treatment. With this configuration, the stent 100 may take the set shape, such as that shown in FIG. 6, in the absence of applied forces. To deliver the prosthetic heart valve 10, the prosthetic heart valve 10 may be collapsed to a small diameter and positioned within a delivery catheter to be passed intravascularly through the patient into the patient's heart. FIG. 7 shows the cut pattern of a portion of stent 100.

Referring collectively to FIGS. 6-7, the stent 100 may be formed with a plurality of rows of generally diamond-shaped cells. In the illustrated example, the atrial disk 110 includes an inflow row of cells 112, which may include a total of twelve cells. A pin 114 may be formed at the inflow apex of one, some, or each cell 112, the pin extending a short distance in the outflow direction to a free end. Each pin 114 may be sized and shaped so that a suture loop of the delivery device may slip over the pin 114, keeping the stent 110 connected to the delivery device during delivery and deployment. Upon deployment of the prosthetic heart valve 10, each suture loop may be pushed forward or distally to disengage with the corresponding pins 114 to fully decouple the prosthetic heart valve 10 from the delivery device. Similar pins and suture loops are described in more detail in U.S. Pat. No. 10,874,512, the disclosure of which is hereby incorporated by reference herein.

A transition row of cells 116 may be positioned directly adjacent to the inflow row of cells 112, with cells 116 transitioning between the atrial disk 110 and the central portion 130. In the illustrated embodiment, a total of twelve atrial transition cells 116 are provided. The central portion 130 may be generally formed by a row of central cells, although each central cell may not be identical to each other central cell. In the illustrated example, there are a total of twelve central cells, with a total of nine connected central cells **132*a*, and three free central cells 132*b*. Each connected central cell 132*a* may be diamond-shaped and have both inflow and outflow apices of the central cell 132*a* connected directly to another cell of the stent. Each free central cell 132*b* may have an inflow apex coupled directly to the outflow apex of an inflow cell 112, with the outflow apex of the free central cell 132*b* transitioning into a CAF 140. With this configuration, there are three free central cells 132*b* evenly spaced around the circumference of the stent 100, and three consecutive connected central cells 132*a* positioned between each pair of free central cells 132*b*. In the illustrated embodiment, each CAF 140 is cantilevered in the sense that it is only coupled to the stent 100 on one side, via two struts of the corresponding free central cell 132*b*. This cantilevered configuration may allow for greater leaflet height while maintaining a relatively small distance between the atrial disk 110 and the ventricular disk 120. The cantilevered configuration may also allow for greater deflection of the CAFs 140 during normal operation of the prosthetic heart valve 10, which may reduce stress on the prosthetic leaflets 500. Each CAF 140 may include one or more eyelets to assist in suturing or otherwise coupling the commissures of the prosthetic leaflets 500 to the CAFs 140. Each CAF 140 may also include a separate fabric coupled to the CAF 140 to assist with suturing of the prosthetic leaflets 500 to the CAF 140. In the illustrated embodiment, each CAF 140 includes a two-by-two array of four small eyelets, with a larger eyelet positioned between the array of four small eyelets and the two struts of the free central cell 132*b*. However, other configurations of eyelets and other types of CAFs may be suitable as an alternative to CAF 140**.

Still referring to FIGS. 6-7, a row of ventricular transition cells 122 may be positioned directly adjacent to the central cells. In the illustrated embodiment, there are a total of six ventricular transition cells 122 provided in pairs, with each ventricular transition cell 122 positioned between two adjacent connected central cells 132. In this example, there are no ventricular transition cells 122 directly adjacent to the free central cells **132*b*. The ventricular transition cells 122 may form part of the cylindrical central portion 130, and flare outwardly to form part of the ventricular disk 120. In the illustrated embodiment, the final ventricular row of cells includes small ventricular cells 124*a* and large ventricular cells 124*b*. For example, a total of nine small ventricular cells 124*a* may be provided, each with an inflow apex directly connected to the outflow apex of a connected central cell 132*a*. Between each series (e.g., series of three) small ventricular cells 124*a*, a large ventricular cell 124*b* is positioned. Portions of the free central cells 132*b*, including the CAFs 140, may nest within the large ventricular cell 124*b* when the stent 100 is collapsed. Thus, in the illustrated embodiment, a total of three large ventricular cells 124*b* are provided. Although one specific configuration of cells is shown and described in connection with FIGS. 6-7, it should be understood that other configurations of cells may provide for suitable functionality of the prosthetic heart valve 10. With the embodiment described above, the stent 100 may be formed as a single unitary or monolithic structure that, when expanded or deployed, has an hourglass-type shape with two opposite disks having a large diameter for anchoring on the atrial and ventricular sides of the native annulus, with a generally cylindrical center portion extending therebetween having a significantly smaller diameter than the disks. As is explained in greater detail below, the central portion 130 of the stent 100 may be positioned a spaced distance from the native annulus after implantation, which is generally in contrast to typical valves where there is stent structure pushing directly against the native annulus tissue after the prosthetic heart valve is implanted. Rather, as described below, the first fabric 200 directly contacts the native annulus tissue upon implantation, with space remaining between the first fabric 200 and the central portion 130 of the stent 100. By avoiding having two separate stents that overlap and increase the bulk of the prosthetic heart valve when collapsed into a delivery device, prosthetic heart valve 10** may be collapsed into a catheter for delivery, the catheter having an inner diameter of smaller than 30 French, including for example 28 French or 24 French or even smaller. Other benefits of this single stent design may include lower cost, and feasible retrieval of the prosthetic heart valve, as a connector between two nested stents might make retrievability more difficult compared to a single stent design.

Referring briefly back to FIGS. 1-3, to allow for the stent 100 to collapse into the delivery device and then expand upon deployment, the outer fabric is preferably designed to not overly restrict the stent 100 from collapsing and expanding. For example, sealing fabrics provided on stents of prosthetic heart valves are frequently woven fabrics and are often tightly sutured or otherwise coupled to the stent so that the fabric does not have the ability to significantly stretch or deviate from its position relative to the stent. Further, these fabrics are often designed with sealing against blood flow as a primary fabric characteristic. On the contrary, prosthetic heart valve 10 has an outer fabric that is capable of significant stretching to accommodate the change in the shape of the stent 100 during transitioning between the collapsed and expanded conditions, with the fabric being spaced a significant distance from the central portion 130 when the prosthetic heart valve 10 is deployed. For example, referring to FIG. 1, when the prosthetic heart valve 10 is deployed into the native valve annulus, the atrial disk 110 and ventricular disk 120 may generally wrap around the atrial and ventricular sides of the native valve annulus, with the outer fabric pressing against the native valve annulus (e.g., via systolic pressure against the fabric on the outflow side), and the central portion 130 of the stent 100 generally centered within (but not directly pressing against) the tissue of the valve annulus. This configuration may allow the central portion 130 of the stent 100 to be a smaller size (e.g., about 28 mm to 32 mm) which may be optimal for hemodynamics, without needing to add additional stent structure to allow for proper sealing and/or anchoring in the much larger sized tricuspid valve annulus. This, in turn, may allow for the prosthetic heart valve 10 to collapse down to a small size for loading into a relatively small delivery device to minimize the likelihood of procedural complications (in particular vascular access complications) resulting from the size of the delivery device. The outer fabric may be formed as a single piece of knit fabric that allows for stretching in one direction, with the ability to seal against the native anatomy and for blood to quickly clot into the fabric to reduce the likelihood of paravalvular ("PV") leak past the prosthetic heart valve 10 after implantation. However, in other embodiments, such as shown in FIG. 1, the outer fabric may include a first fabric 200 that is formed of a material chosen for its ability to stretch (e.g. a knit fabric), and a second fabric 300 at the atrial disk 110 and ventricular disk 120 that is chosen for the sealing, ingrowth, and/or clotting properties (e.g. a woven fabric), with the first fabric 200 coupled to the second fabric 300 in any desired fashion that allows the stretching to occur.

Although prosthetic heart valve 10 is described above with a particular frame or stent 100, and a particular configuration of sealing fabrics (e.g., first fabric 200 and second fabric 300), it should be understood that these are merely exemplary configurations and other configurations may be suitable. For example, additional configurations of the frame and sealing fabric are described in greater detail in U.S. Provisional Patent Application No. 63/341,702, filed May 13, 2022, and titled "Transcatheter Valve—Single Stent Structure With Fabric," the disclosure of which is hereby incorporated by reference herein.

Figure 8A:
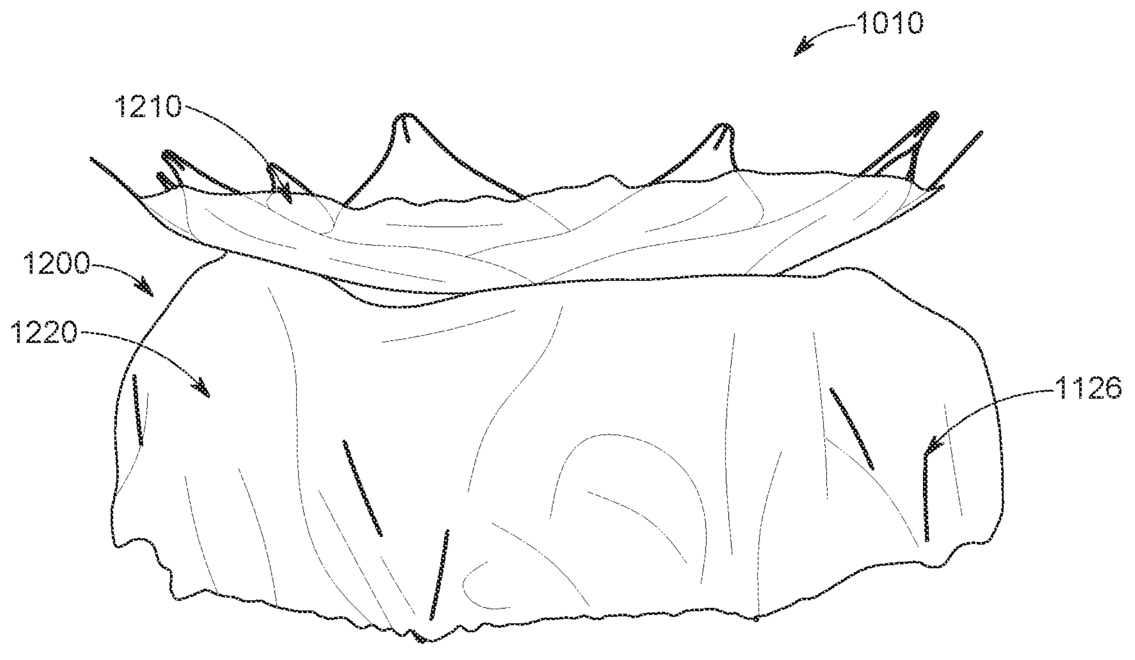
FIG. 8A is a perspective view of a prosthetic heart valve having a configuration different than the prosthetic heart valve of FIGS. 1-7.

FIG. 8A illustrates a prosthetic heart valve 1010 according to another embodiment of the disclosure. As with prosthetic heart valve 10, prosthetic heart valve 1010 may be particularly suited for replacing a native atrioventricular valve, and in particular the native tricuspid valve. Prosthetic heart valve 1010 may include three components generally, including a stent or frame 1100, a sealing skirt 1200, and prosthetic leaflets 1500. Prosthetic heart valve 1010 is shown in FIG. 8A in an expanded or deployed condition and is oriented with the atrial or inflow end of the valve toward the top of the view of FIG. 8A.

Figure 8B:
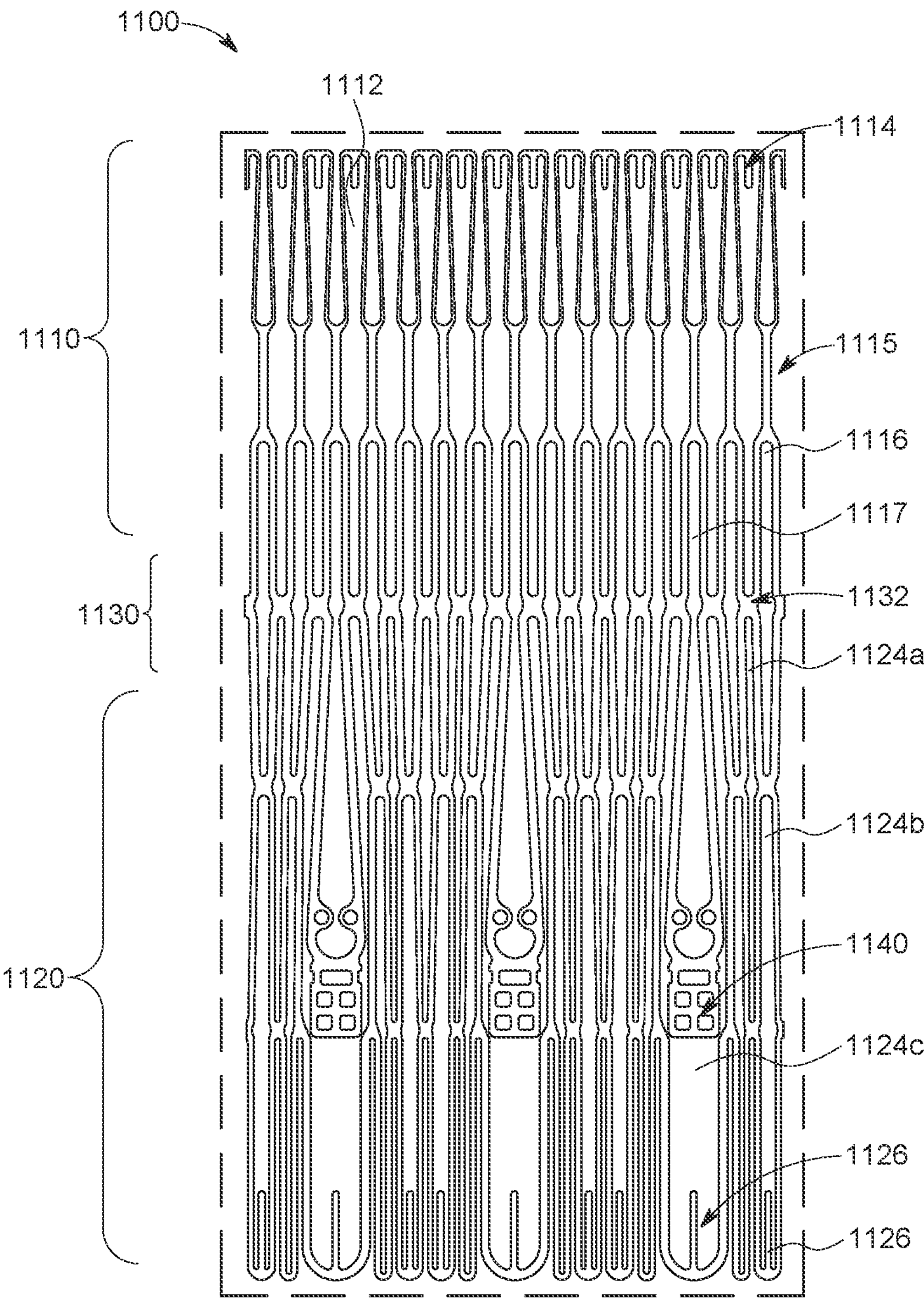
FIG. 8B is a view of a cut pattern of a stent for use with the prosthetic heart valve of FIG. 8A.

FIG. 8B illustrates a cut pattern of a stent of frame 1100 that may be used with prosthetic heart valve 1010. In FIG. 8B, the frame 1100 has the same orientation as shown in FIG. 8A. In other words, in the views of FIGS. 8B-C, the inflow or atrial end of the frame 1100 is oriented toward the top of the view. Frame 1100 is preferably formed from a shape-memory material, such as a nickel-titanium alloy such as Nitinol, and may be created from a single tube, for example via laser cutting a tube of Nitinol. In the cut patterns shown in FIG. 8B, the frame 1100 generally includes an atrial portion 1110 and a ventricular portion 1120 separated by a center portion 1130. After the frame 1100 is cut and set to the desired shape, for example as shown and described in greater detail in connection with FIG. 8C, the center portion 1130 may be very short, particularly in comparison to the center portion 130 of frame 100 shown in FIGS. 1-2.

Frame 1100 may include an atrial-most or inflow-most row of atrial cells 1112, which may be generally diamond-shaped cells that, in the expanded condition, flare radially outwardly from the center portion 1130. A pin 1114 may be formed at the inflow apex of one, some, or each atrial-most cell 1112, the pin 1114 extending a short distance in the outflow direction to a free end. Each pin 1114 may be sized and shaped so that a suture loop of the delivery device may slip over the pin 1114, keeping the frame 1100 connected to the delivery device during delivery and deployment. Upon deployment of the prosthetic heart valve 1010, each suture loop may be pushed forward or distally to disengage with the corresponding pins 1114 to fully decouple the prosthetic heart valve 1010 from the delivery device. Similar pins and suture loops are described in more detail in U.S. Pat. No. 10,874,512, the disclosure of which is hereby incorporated by reference herein. The atrial cells 1112 may terminate, at their outflow ends, at an inflection point 1132. When the frame 1100 is shape-set to the desired shape, which may be generally similar to that shown in FIG. 8C, the inflection points 1132 may define the smallest diameter of the center portion 1130. It should be understood that the term "inflection point" is not necessarily used according to its mathematical definition, but rather references the point at which the frame 1100 changes from decreasing diameter to increasing diameter.

Still referring to FIG. 8B, a plurality of transition cells 1116, which may be generally diamond-shaped, may be positioned in a row that is adjacent to the atrial cells 1112 in the outflow direction. Transition cells 1116 may include an inflow portion on the inflow side of center portion 1130 and an outflow portion on the outflow side of center portion 1130. In some examples, the transition cells 1116 may be axially centered about the inflection point 1132. The row of transition cells 1116 may include three enlarged transition cells 1117 (or more or fewer than three depending on the number of prosthetic leaflets included in the prosthetic heart valve 1010) that terminate in a commissure attachment feature ("CAF") 1140. Preferably, the enlarged transition cells 1117 are positioned at substantially equal circumferential intervals around the frame 1100. As best shown in FIG. 8B, the sides of the atrial cells 1112 (which may extend to the inflow apex of the transition cells 1116 and the enlarged transition cells 1117) may include elongated beams 1115. These elongated beams 1115 may provide additional flexibility to the atrial portion 1110 (which may be referred to as the atrial disk).

Figure 8C:
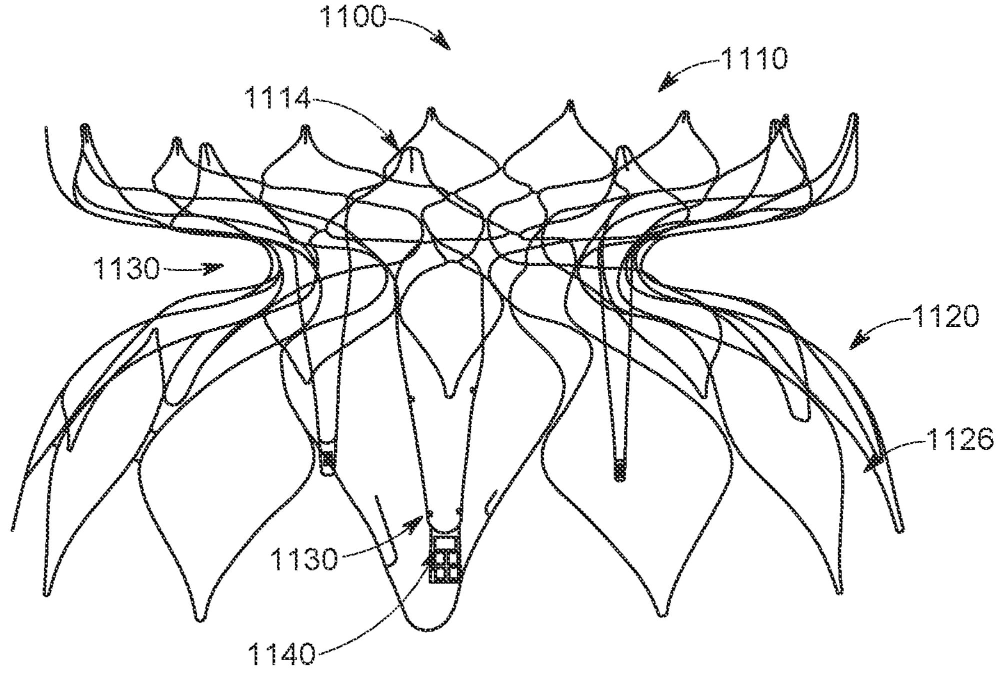
FIG. 8C shows the prosthetic heart valve of FIG. 8A with certain structures omitted from the view for clarity.

Each CAF 1140 may serve as an attachment point to the prosthetic leaflets, which are not shown in FIGS. 8A-C but which may be substantially similar or identical to prosthetic leaflets 500. For example, each CAF 1140 may include a plurality of holes, and sutures may be used to couple adjacent pairs of leaflets to the CAFs 1140 via the holes therein. While CAFs 1140 are shown with four small holes in a two-by-two configuration and an elongated hole, other specific CAF configurations may be suitable for use instead of those shown.

The portion of the frame 1100 in the outflow direction of the inflection point 1132 may include a plurality of ventricular cells. For example, a group of first ventricular cells **1124*a* which may be generally diamond-shaped cells, the inflow apex of which is an inflection point 1132. A group of second ventricular cells 1124*b* may extend to the outflow-most portion of the frame 1100, the inflow apices of the second ventricular cells being connected to the outflow apices of the transition cells 1116. Some, none, or all of the second ventricular cells 1124*b* may include tines 1126 that may function as frictional engagement members that frictionally engage native tissue for enhancing securement of the frame 1100 within the native valve annulus. A group of third ventricular cells 1124*c* may be positioned between certain pairs of second ventricular cells 1124*b*, and may include struts that extend from the inflection point 1132 to the terminal outflow end of the ventricular portion 1120. Third ventricular cells 1124*c* may be larger than the other ventricular cells and may be formed in part by the struts of enlarged transition cells 1117 that terminate at CAFs 1140. With this configuration, at least in the cut pattern shown in FIG. 8B, the CAFs 1140 may be thought of as either nested within third ventricular cells 1124*c* or forming a boundary of third ventricular cells 1124*c***.

In addition to tines 1126 being positioned in some, none, or all of the second ventricular cells **1124*b*, none, some, or all of the third ventricular cells 1124*c* may include tines 1126. As shown in FIG. 8C, each third ventricular cell 124*c* may include a single tine 1126 extending upward from an outflow apex of the cell. Some of the second ventricular cells 1124*b* may also include tines 1126, such that each second ventricular cell 1124*b* that includes a tine 1126 includes a single tine 1126 extending upward from an outflow apex of the cell. All of the tines 1126 may extend to a free tip that may have a sharp or blunt point, that is intended either to pierce tissue or to frictionally engage the tissue without piercing it. It should be understood that the number and positioning of the tines 1126 may be different from those shown in FIG. 8B, and the specific number and positioning shown in FIG. 8**B is merely exemplary.

In the illustrated embodiments, the tines 1126 may be connected at an outflow end of the tine, with the free tip being positioned at an inflow end of the tine. This directionality of tines, compared to the tines being connected at their inflow end and having free tips at their outflow ends, may allow for a smoother and easier deployment of the valve from the delivery catheter. In other words, as the valve begins to self-expand as it is released from the delivery catheter, the tines do not begin to expand until the entire tine is free of the delivery device. With the opposite orientation, the tines might otherwise begin to extend radially outwardly and into contact with the end of the delivery sheath, which might make deployment more difficult. However, it should be understood that the illustrated directionality of tines may make the loading process slightly more difficult compared to the opposite directionality. However, smooth and easy deployment is typically more important than smooth and easy loading, and the loading process can be highly controlled and is performed outside the patient, while the deployment process is performed inside the patient.

After forming the frame 1100 by using the cut pattern shown in FIG. 8B, or another generally similar cut pattern, the frame 1100 may be shape-set, for example via heat treatment, to the desired shape. FIG. 8C illustrates one example of a frame 1100 that has a cut pattern similar to that shown in FIG. 8B, after having been shape set.

As can be seen in FIG. 8C, when the frame 1100 is in the expanded or deployed condition the bottom of the atrial portion 1110 may be substantially straight with a slight upward angle, while the top half of the atrial portion 1110 may flare upwardly so that the tips of the atrial cells 1112 point generally in the inflow direction. The contours described above may be other than as exactly described while still being suitable for use in the prosthetic heart valve 1010.

Still referring to FIG. 8C, the ventricular portion 1120 may form a general "bell" shape with a more rounded and less flat contour compared to the atrial portion 1110. The more gentle contour of the ventricular portion 1120 may allow for the ventricular portion 1120 to drape against the ventricle and apply only light pressure to assist in fixing or otherwise securing the prosthetic heart valve 1010 to the native valve annulus. This light pressure or draping may be a first mechanism by which the prosthetic heart valve 1010 achieves fixation within the native valve annulus.

The various tines 1126 described above may be shape set so that the free ends of the tines 1126 are positioned away from the surfaces defined by the cell in which the tine 1126 is located. In other words, the tines 1126 may be bent or shaped so that the tips are available to pierce tissue or to frictionally engage tissue without piercing to provide a second mechanism by which the prosthetic heart valve 1010 achieves fixation within the native valve annulus. The tines 1126 may be oriented at different angles to achieve different objectives. For example, in some embodiments, some or all of the tines 1126 may be oriented or angled with the free ends pointing toward the atrial portion 1110 at an acute angle relative to the longitudinal axis passing through the center of the prosthetic heart valve 1010. Tines 1126 pointing at an acute angle, compared to a right angle or an obtuse angle, may be less likely to perforate tissue at the native valve annulus. Patients that may need a prosthetic atrioventricular valve, particularly a prosthetic tricuspid valve, may be likely to have very thin medial walls in the ventricle, and acutely angled tines 1126 may particularly reduce the likelihood of the medial wall getting perforated by the tines 1126. There may be additional benefits to having an acutely angled tine 1126 compared to tines 1126 with larger angles (e.g., right angle or obtuse angle), relating to loading and deployment of the prosthetic heart valve 1010. For example, if the tines 1126 are more acutely angled, they may provide less resistance when the prosthetic heart valve 1010 is loaded into, or deployed from, the delivery catheter. Less resistance may equate to a more manageable load, which—all else being equal—may allow for a smaller size delivery catheter to be used. However, this is just one option. Some or all of the tines 1126 may instead be shape set to be oriented more laterally, for example a relatively large acute angle, or a right or obtuse angle, relative to the central longitudinal axis of the prosthetic heart valve 1010. Although the tines 1126 may be optional entirely, if the tines 1126 are included, whether they are acutely or laterally oriented, the tines 1126 may provide a second mechanism by which the prosthetic heart valve 1010 achieves fixation within the native valve annulus.

Referring again to FIG. 8A, an outer sealing skirt 1200 may be provided on the exterior of the frame 1100. In some embodiments, the sealing skirt 1200 may be the same as or similar to any of the embodiments described above. In the particular example shown in FIG. 8A, the sealing skirt 1200 may be a single piece of material (although in some embodiments it may be a multi-piece design), which may be any of the materials described in connection with the sealing skirts above, including for example woven PET. In the illustrated embodiment of FIG. 8A, the sealing skirt 1200 may have an atrial skirt portion 1210 and a ventricular skirt portion 1220. The atrial skirt portion 1210 may be coupled to the atrial portion 1110 of the frame 1100 with a relatively tight connection—for example via suturing along the struts of the atrial portion 1110 of the frame 1100. In some embodiments, including that shown in FIG. 8A, the inflow edge of the atrial skirt portion 1210 may be positioned a spaced distance from the atrial tips of the atrial cells 1112. In other embodiments, the inflow edge of the atrial skirt portion 1210 may be positioned to align with or cover the atrial tips of the atrial cells 1112. It should be understood that the various tines 1126 preferably pierce or otherwise extend through the sealing fabric 1200 so that the free ends thereof are available for frictional engagement with the native tissue upon implantation.

Still referring to FIG. 8A, the ventricular skirt portion 1220 may be more loosely connected to the ventricular portion 1120 of the frame 1100 than the atrial skirt portion 1210 is connected to the atrial portion 1110. For example, the outflow edge of the ventricular skirt portion 1220 may be relatively tightly coupled to the outflow end of the ventricular portion 1120 of the frame 1100, but the connection of the sealing skirt 1200 may be relatively loose between the central portion 1130 and the terminal end of the ventricular portion 1120 of the frame 1100. With this configuration, during ventricular systole (e.g., as the ventricle contracts, the prosthetic leaflets close, and the pressure in the ventricle is greater than the pressure in the atrium), the pressure differential causes the ventricular skirt portion 1220 to billow, inflate, or parachute open. As the ventricular skirt portion 1220 parachutes during ventricular systole, it may fill any gaps, crevices, or openings between the prosthetic heart valve 1010 and the native valve annulus that might otherwise result in blood leaking around the outside of the prosthetic heart valve 1010 back into the atrium (i.e., PV leak).

Referring briefly to FIG. 8C, the illustrated configuration of frame 1100 may provide a levering effect that may further assist with sealing against PV leak. For example, when the frame 1100 is in the expanded or deployed state shown in FIG. 8C, deformation of the ventricular portion 1120 may tend to lever the atrial portion 1110 toward the ventricular portion 1120. Thus, referring back to FIG. 8A, as the ventricular skirt portion 1220 inflates or parachutes during ventricular systole, which may cause the ventricular portion 1120 of the frame 1100 to slightly deform, the atrial portion 1110 of the frame 1100 may be lightly pulled downward against the atrial side of the native valve annulus. This "sandwiching" action may further seal against any PV leak, and may also mitigate potential embolization. For example, particularly in the low-flow environment of the right heart, any gaps or spaces left between the prosthetic heart valve 1010 and the native anatomy may create a thrombus risk zone. The above-described levering or sandwiching effect may reduce or eliminate any such gaps or spaces, thus reducing the risk of thrombus formation. In one particular example, patients may have a pronounced septal bump, and some patients may have in particular a septal bump in the right ventricle that overhands the tricuspid valve annulus. This anatomy may be an exclusion criterion for a transcatheter prosthetic tricuspid valve replacement. However, the sandwiching or levering effect described above may allow for prosthetic heart valve 1010 to be implanted into patients who have relatively pronounced septal bumps.

Referring again to FIG. 8C, in the deployed or expanded condition of the frame 1100, the bottom struts of the enlarged transition cells 1117, to which the CAFs 1140 are connected, extend in the outflow direction substantially parallel to the central longitudinal axis of the prosthetic heart valve 1010. With this positioning, the CAFs 1140 may be positioned in alignment with, or nearly in alignment with, the smallest diameter portion of the frame 1110 at the central portion 1130. In other words, the CAFs 1140 of frame 1100 are effectively cantilevered.

One potential issue with the frames 100 and/or 1100 described above is that forces applied to one end of the frame may be too readily transmitted to the other end of the frame. This force transmission may be a result of the direct connection of diamond-shaped cells without any intervening structure or the inclusion of structures such as beams 1115 between cells. In prosthetic heart valves that include two nested frames, the two frames may be connected to each other in a way that dampens forces so that forces applied to an outer frame dissipate or are otherwise absorbed before reaching the inner frame. This force absorption, dissipation, or dampening may help ensure that the inner frame (which carries the prosthetic leaflets) does not significantly change shape despite distortions on the outer frame, which may be caused by the native annulus applying forces on the outer frame during the cycle of the heart. However, with a single-frame design as disclosed herein, the same force-dampening mechanisms may not be possible as are possible with a nested or double-frame device.

Figure 9A:
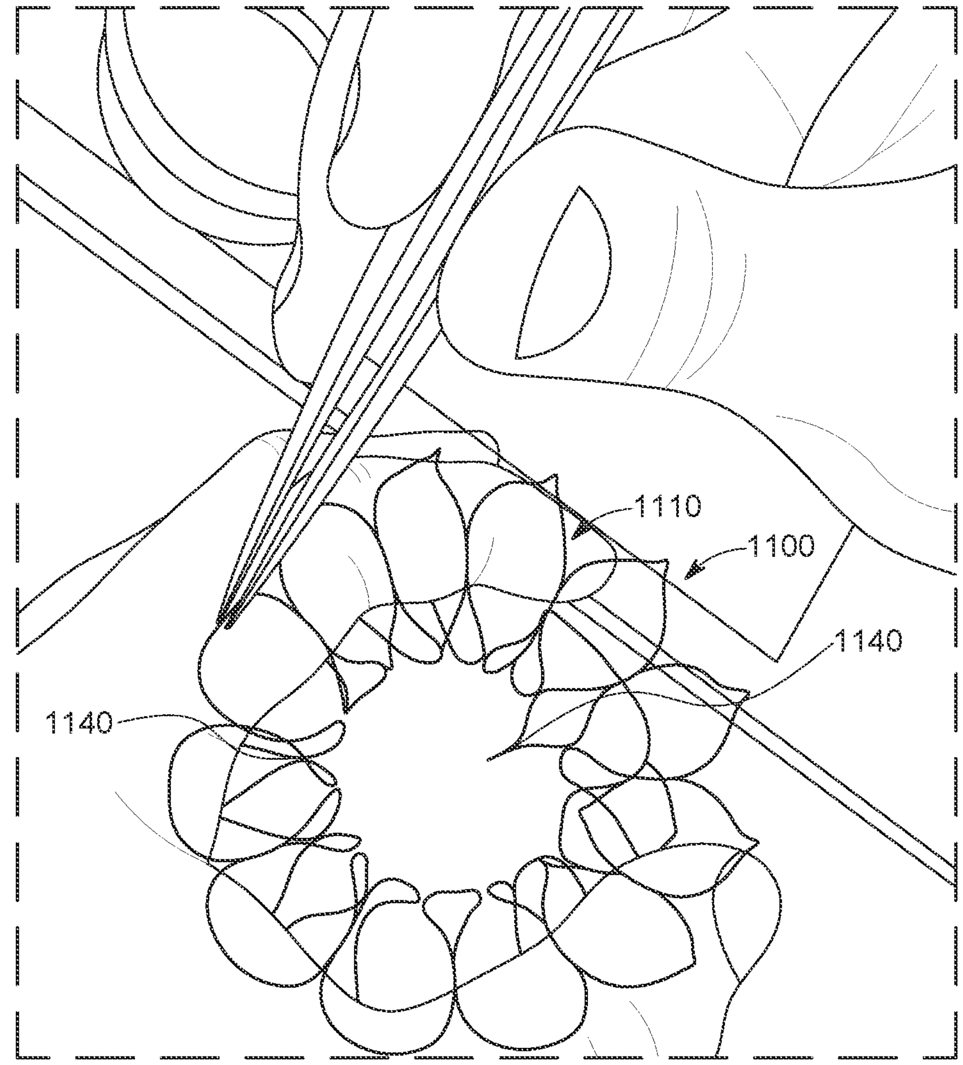
FIGS. 9A-B illustrate the frame of FIG. 8C before and after, respectively, radially inward force is applied to an atrial cell of the frame.

FIG. 9A shows frame 1100 being held while in an expanded or deployed condition, with the atrial portion 1110 being in the foreground in the view of FIG. 9A. In FIG. 9A, forceps or tweezers are gripping the tip of an atrial cell 1112, but little or no force is being applied to the frame 1100, so that the frame 1100 generally has the shape shown in FIG.

Figure 9B:
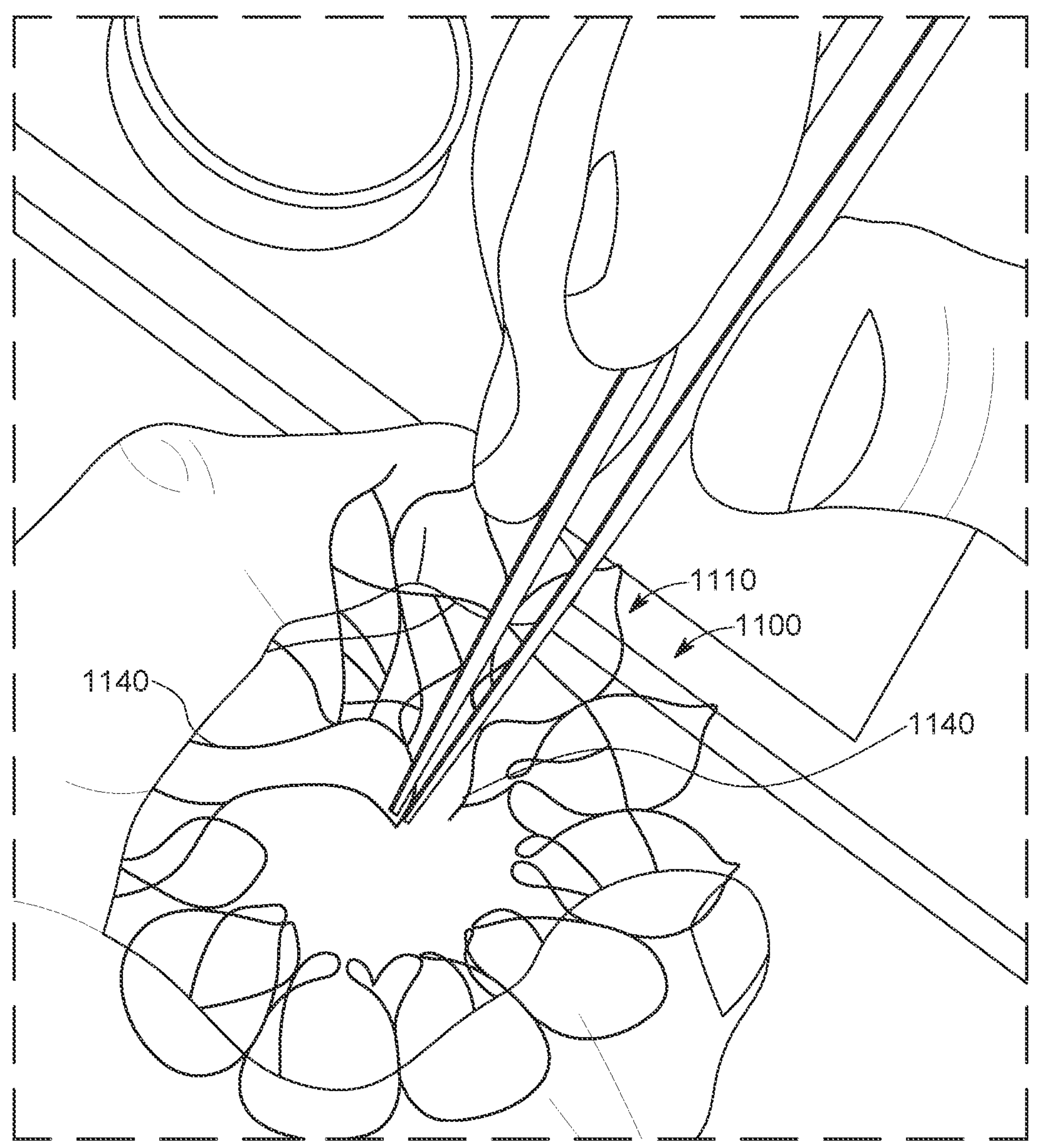

8C. However, FIG. 9B illustrates frame 1100 with the forceps having pulled the atrial portion 1110, at the tip of an atrial cell 1112, radially inward toward the center of the valve. The motion occurring between the positions shown in FIGS. 9A and 9B may be thought of as exaggerated atrial movement (e.g., right atrial movement if frame 1100 is for a prosthetic tricuspid valve). As can be seen by comparing FIGS. 9A and 9B, as the atrial cell 1112 is forced radially inwardly, a "crow-bar" effect occurs in which the ventricular section that is aligned axially with the moving atrial cell 1112 moves in the opposite direction. In other words, as shown in FIG. 9B, the CAF 1140 that is axially aligned with the atrial cell 1112 being manipulated moves significantly radially outwardly (e.g., is "kicked out") as the atrial cell 1112 moves radially inwardly. This occurs because the forces are too readily transmitted from the atrial cells to the CAF 1140, although such motion may be generally localized in the sense that the other CAFs 1140 are not significantly affected by the movement of the illustrated atrial cell 1112. It should be clear the motion of the CAFs 1140 is typically not desirable, because it is this portion of the frame to which the prosthetic leaflets are directly connected. Stated in another way, if frame 1100 were part of a prosthetic tricuspid valve implanted in the right heart, and if the tricuspid valve annulus exerted pressure on the atrial portion 1110 of the frame 1100, it could cause the ventricular portion 1120, and particularly one or more CAFs 1140, to move so that the CAFs 1140 are no longer in a generally cylindrical profile. This movement, in turn, might change the shape of the assembled prosthetic leaflets, creating a situation in which coaptation is not occurring properly and blood is flowing from the right ventricle to the right atrium during ventricular systole. And although the deformation of the atrial portion 1110 of the frame 1100 is described as being potentially caused by normal cycling of the heart between systole and diastole, it may separately and/or additionally be caused by a complex and/or irregular shape of the native valve annulus and/or irregular shape of the atrium, irrespective of movements attributable to the cardiac cycle.

It should be noted that, although the frame shown in FIGS. 9A-B is labeled as frame 1100, it includes a CAF 1140 that is closer in construction to CAF 2140 than the CAF shown in FIGS. 8A-C. And while this potential problem is described in connection with frame 1100, it should be understood that the potential problem may exist for various other designs of prosthetic heart valve frames, particularly ones that include only a single frame for both (i) anchoring and (ii) supporting a prosthetic leaflet assembly.

Figure 10A:
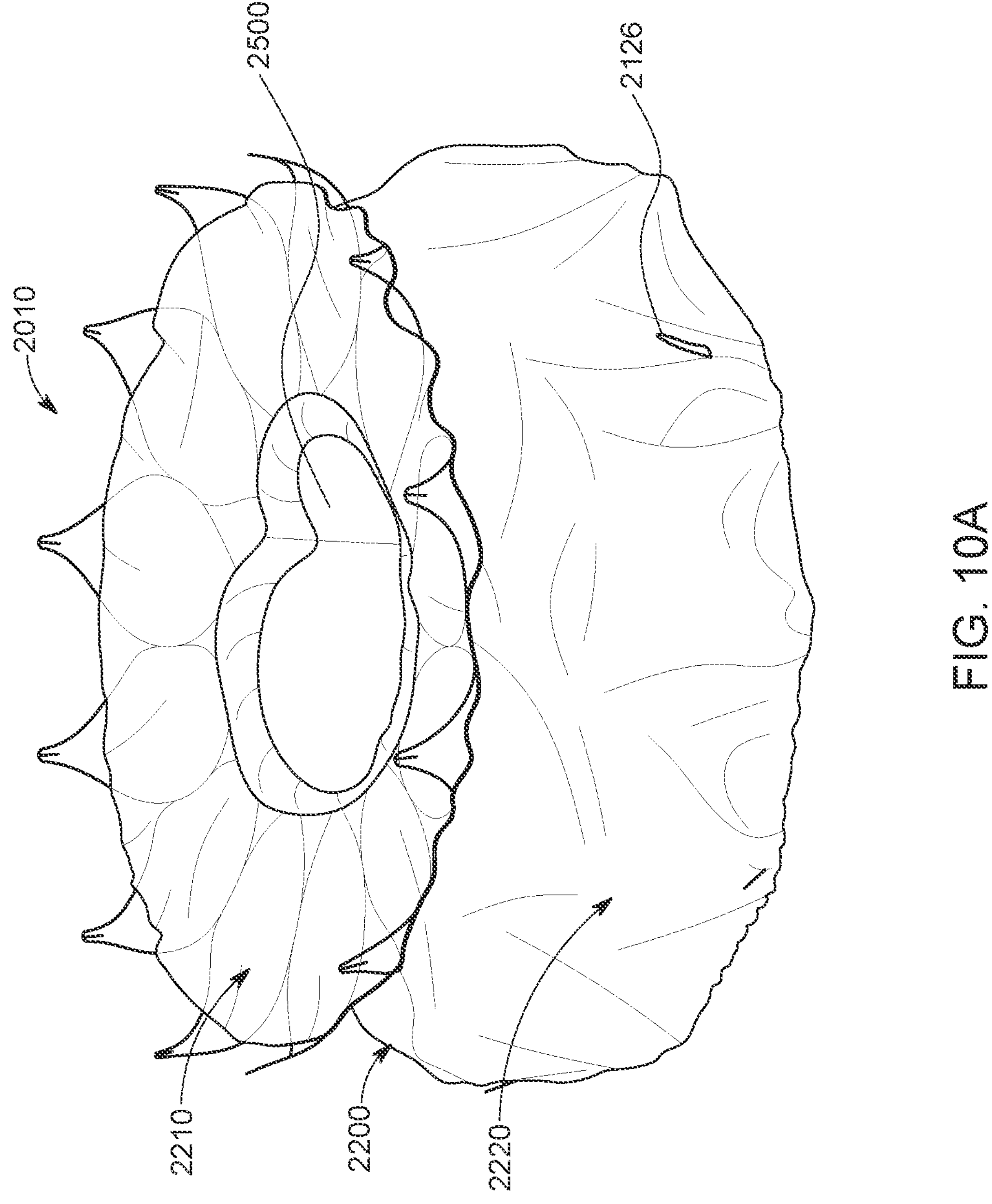
FIG. 10A is a perspective view of a prosthetic heart valve, in an expanded or deployed condition, according to an aspect of the disclosure.

FIG. 10A illustrates a perspective view of a prosthetic atrioventricular heart valve 2010 in an expanded or deployed condition. Prosthetic heart valve 2010 may be substantially similar to prosthetic heart valve 1010, with one exception being features of frame 2100 that may assist in "breaking" force from being translated between the atrial section 2110 and ventricular section 2120 of the frame 2100. It should be understood that certain features of prosthetic heart valve 2010 may not be described herein in detail, and it should be understood that, unless explicitly noted otherwise, the features described and shown in connection with prosthetic heart valve 1010 may apply with similar or equal force to prosthetic heart valve 2010. Prosthetic heart valve 2010 may include three main components, including the frame 2100, a sealing skirt 2200, and prosthetic leaflets 2500. The sealing skirt 2200, which may include an atrial portion 2210 and a ventricular portion 2220, may be substantially similar or identical to sealing skirt 1200, and is thus not described in more detail again here. Similarly, the prosthetic leaflets 2500 may be similar or identical to prosthetic leaflets 500 and/or the prosthetic leaflets described in connection with prosthetic heart valve 1010. Thus, the prosthetic leaflets 2500 are not described in greater detail herein.

Figure 10B:
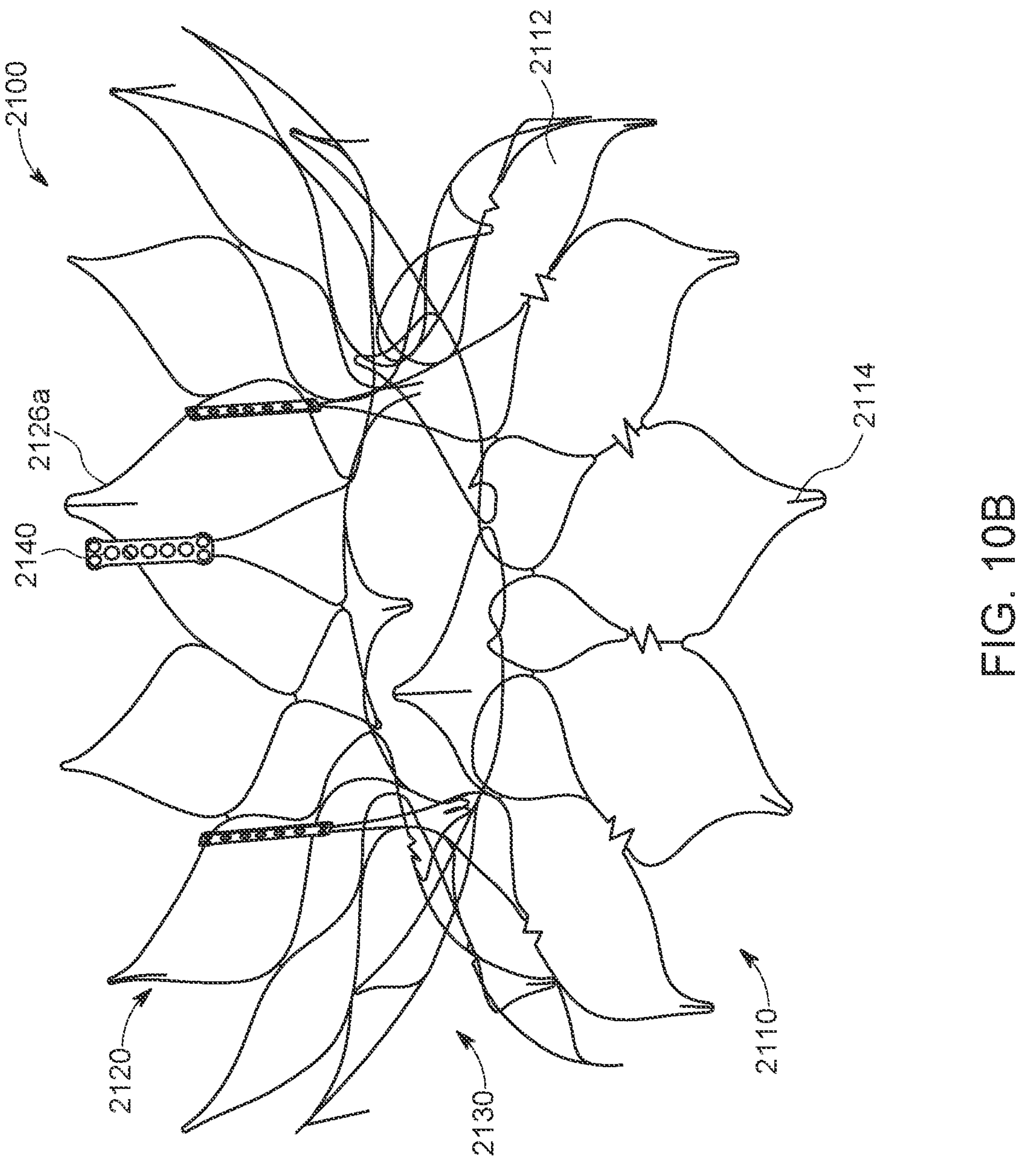
FIG. 10B is a perspective view of the frame of FIG. 10A in an expanded or deployed condition.
Figure 10C:
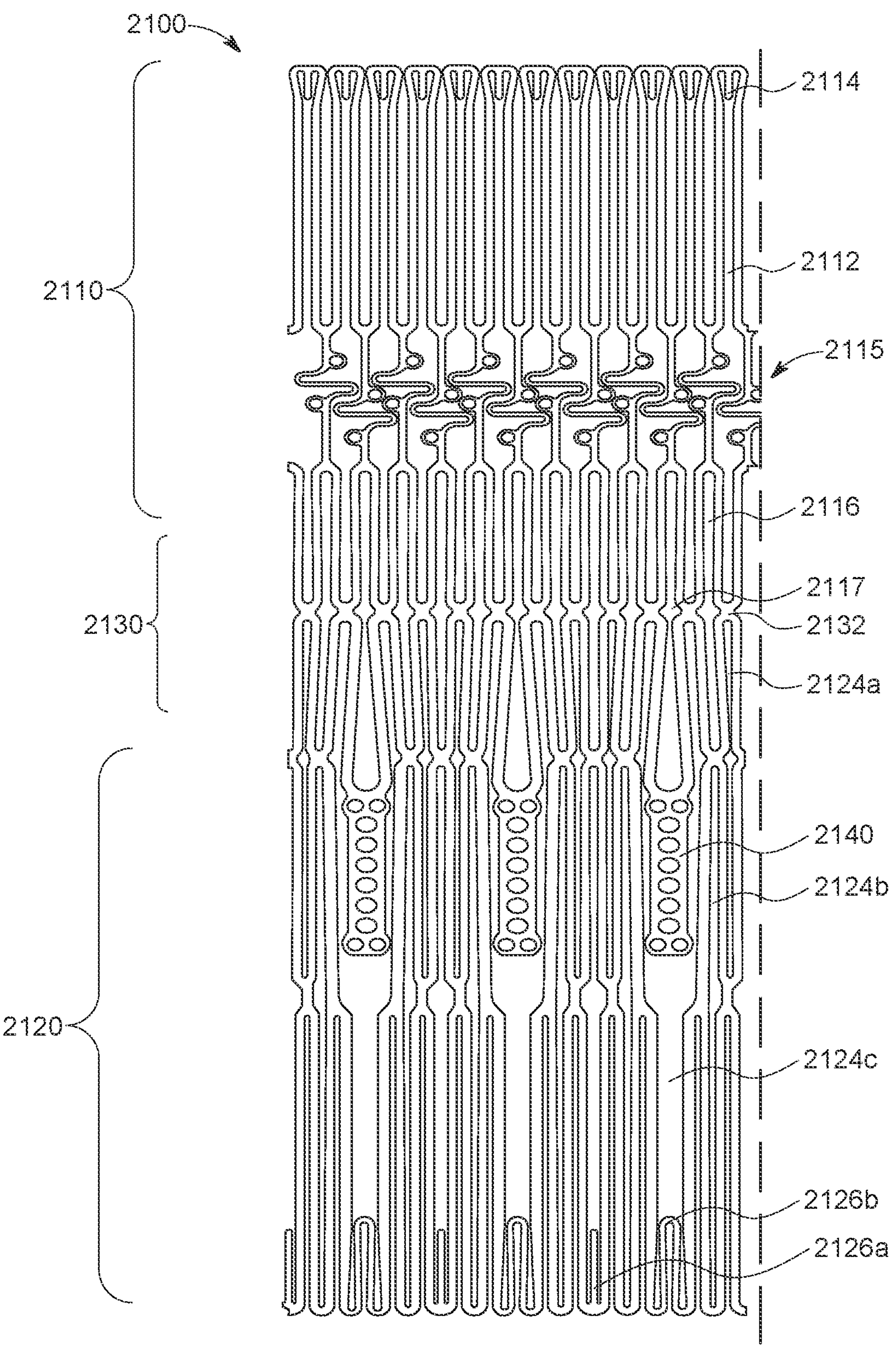
FIG. 10C illustrates a cut pattern for the frame of FIG. 10B.

FIG. 10B illustrates the frame 2100 in an expanded or deployed condition, with all other components of the prosthetic heart valve 2010 omitted. FIG. 10C illustrates the cut pattern for frame 2100. It should be understood that FIG. 10B illustrates the frame 2100 with the ventricular or outflow side toward the top of the view, while FIG. 10C (along with FIG. 10A) illustrates the frame 2100 with the atrial or inflow side toward the top of the view. Frame 2100 is preferably formed from a shape-memory material, such as a nickel-titanium alloy such as Nitinol, and may be created from a single tube, for example via laser cutting a tube of Nitinol. In the cut patterns shown in FIG. 10C, the frame 2100 generally includes an atrial portion 2110 and a ventricular portion 2120 separated by a center portion 2130. After the frame 2100 is cut and set to the desired shape, for example as shown in FIG. 10B, the center portion 2130 may be very short, particularly in comparison to the center portion 130 of frame 100 shown in FIGS. 1-2.

Features of frame 2100 will generally only be briefly described since the corresponding description of frame 1100 may generally also apply, with certain exceptions noted below. Frame 2100 may include an atrial-most or inflow-most row of atrial cells 2112 with pins 2114 formed at the inflow apex of one, some, or each atrial-most cell 2112. The atrial cells 2112 may terminate, at their outflow ends, at an inflection point 2132.

A plurality of transition cells 2116 may be positioned in a row that is adjacent to the atrial cells 2112 in the outflow direction. The row of transition cells 2116 may include three enlarged transition cells 2117 (or more or fewer than three depending on the number of prosthetic leaflets included in the prosthetic heart valve 2010) that terminate in a commissure attachment feature ("CAF") 2140. Each CAF 2140 may serve as an attachment point to a pair of the prosthetic leaflets 2500.

The portion of the frame 2100 in the outflow direction of the inflection point 2132 may include a plurality of ventricular cells, including a group of first ventricular cells **2124*a*, the inflow apex of which is an inflection point 2132. A group of second ventricular cells 2124*b* may extend to the outflow-most portion of the frame 2100, the inflow apices of the second ventricular cells being connected to the outflow apices of the transition cells 2116. A group of third ventricular cells 2124*c* may be positioned between certain pairs of second ventricular cells 2124*b*, and may include struts that extend from the inflection point 2132 to the terminal outflow end of the ventricular portion 2120. Third ventricular cells 2124*c* may be larger than the other ventricular cells and may be formed in part by the struts of enlarged transition cells 2117 that terminate at CAFs 2140. With this configuration, at least in the cut pattern shown in FIG. 10C, the CAFs 2140 may be thought of as either nested within third ventricular cells 2124*c* or forming a boundary of third ventricular cells 2124*c***.

One of the differences between frame 2100 and frame 1100 is that frame 2100 may include slightly different tines **2126*a*, 2126*b*. Tines 2126*a* may be substantially similar in structure to tines 1126 and serve the same purpose. In the illustration of FIG. 10B, every other cell in the ventricular-most row of cells includes a single tine 2126*a* having a first connected end and extending to a second free end. In the illustration of FIG. 10C, each ventricular cell 2124*c* includes a tine 2126*b* that may form a general "U"-shape. In other words, tines 2126***b* have two connected ends that meet at a rounded end that is configured to frictionally engage tissue. In the illustration of FIG. 10C, the middle ventricular cell 2124*b* in each group of three consecutive ventricular cells 2124*b* includes a tine 2126*a*. As with frame 1100, the tines 2126*a* and/or 2126*b* provided with frame 2100 may be provided in different numbers, positions, and/or configurations than shown in FIGS. 10B-C, and may otherwise be omitted entirely. The tines 2126*a* and 2126*b* may be shape set in similar ways as described in connection with tines 1126.

Another one of the differences between frame 2100 and frame 1100 is that the CAFs 2140 of FIGS. 10B-C are provided as substantially longitudinal beams with a single column of holes, although other holes (e.g., pairs of horizontal holes at the two opposite ends of the single column of holes) may be provided. The holes may be used to suture or otherwise connect the prosthetic leaflets 2500 to the frame 2100 at the CAFs 2140. The column of holes may allow for stable attachment to the commissures of the prosthetic leaflets 2500, without any foreshortening of the CAFs 2140 during radial expansion. The pairs of holes on the opposite ends of the column of holes may help stabilize commissure tissue in the axial (or flow) direction. It should be understood that CAFs 2140 may take other configurations, including those shown and described in connection with other embodiments herein, or any other suitable configuration.

Still further, while frame 1100 includes longitudinally extending beams 1115 within the atrial portion 1110 (e.g., forming the "side" struts of each of the atrial cells 1112), frame 2100 includes longitudinally extending beams 2115 that are interrupted by a wave-shaped or undulating portion configured to "break" force transmission along the beams 2115 from the atrial portion 2110 to the center portion 2130 and ventricular portion 2120 (and vice versa). It should be understood that the term "undulating" as used herein is not intended to refer to only one specific structural shape. In other words, although the undulating structure shown and described in greater detail below generally has a sinusoidal or wavy or zig-zag type of shape, as used herein, the term "undulating" refers to any structure that (i) has a shape other than a longitudinal beam and (ii) allows for force dampening across the structure.

Figure 10D:
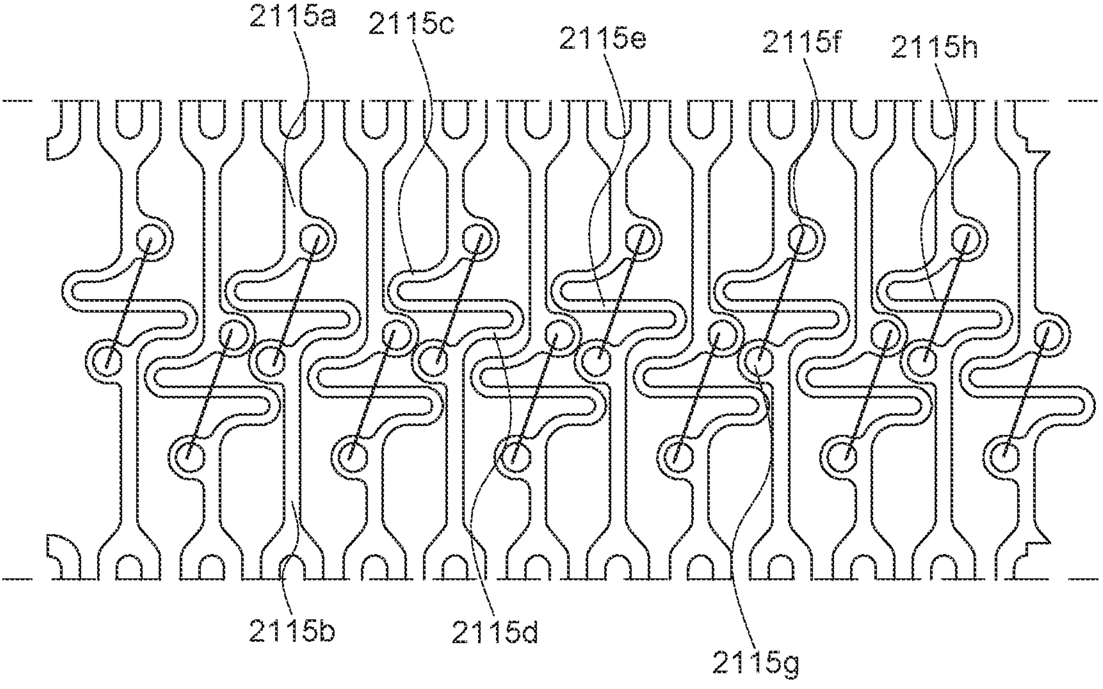
FIG. 10D illustrates a portion of the cut pattern of FIG. 10C.

FIG. 10D illustrates an enlarged view of the beams 2115 of frame 2100. Each beam 2115 may include a first longitudinal beam portion 2115*a* (e.g., toward an inflow-side) and a second longitudinal beam portion 2115*b* (e.g., toward an outflow-side), with the two beam portions 2115*a*, 2115*b* separated by the undulating structure. For a first group of beams 2115, the first longitudinal beam portion 2115*a* may be longer than the second longitudinal beam portion 2115*b*. For a second group of beams 2115, the first longitudinal beam portion 2115*a* may be shorter than the second longitudinal beam portion 2115*b*. The two longitudinal beam portions 2115*a*, 2115*b* may be axially aligned with each other. The two longitudinal beam portions 2115*a*, 2115*b* may be separated by an undulating or wave portion, which may be a generally sinusoidal or other undulating shape. For example, in the illustrated embodiment, each beam 2115 may include a first curved portion 2115*c* that curves generally circumferentially in a first direction from the first beam portion 2115*a*, and a second curved portion 2115*d* that curves generally circumferentially in a second direction, opposite the first direction, from the second beam portion 2115*b*. The two curved portions 2115*c*, 2115*d* may be connected by a generally horizontally or circumferentially extending connector 2115*e*. With the above-described configuration, the undulating structure separating the two longitudinal beam portions 2115*a*, 2115*b* may include at least three portions that extend generally circumferentially (which may be generally orthogonal or perpendicular to the direction in which the longitudinal beam portions 2115*a*, 2115*b* extend). As a result of this undulating portion, axial force transmitted along either of the longitudinal beam portions 2115*a*, 2115*b* will tend to cause the various curved portions 2115*c*, 2115*d* and connector 2115*e* to compress, dampening the force transmission so that little or no force is transmitted from one of the beam portions (2115*a* or 2115*b*) to the other of the beam portions (2115*a* or 2115*b*). It should be understood that, after being shape-set, the frame 2100 is not a flat, generally two-dimensional structure. Thus, although the undulating portions of the beams 2115 may generally compress to "break" (or absorb or dampen) force transmission across the length of the beams 2115, the undulation portions may also move in other dimensions to assist with isolating force applied on the atrial portion 2110 from transmitting to the ventricular portion 2120 (and vice versa).

Still referring to FIG. 10D, the connecting portion 2115*e* may have a length in the horizontal or circumferential direction that is larger than the distance between adjacent first longitudinal beam portions 2115*a* and/or between adjacent second longitudinal beam portions 2115*b*. As a result, the undulating portions could not be provided on every beam 2115 in exactly the same position, otherwise the connecting portions 2115*e* of adjacent beams 2115 would interfere with each other. Thus, in embodiments in which each beam portion 2115 is provided with an undulating structure, each undulating structure may be axially offset from the undulating structure of the adjacent beams 2115. For example, in the embodiment shown in FIG. 10D, every other beam 2115 may include a short first beam portion 2115*a* and a long second beam portion 2115*b*. Each remaining beam 2115 may include a long first beam portion 2115*a* and a short second beam portion 2115*b*. With this configuration, the connecting portion 2115*e* of each beam 2115 may be axially offset from that of an adjacent beam 2115, so that the connecting portions 2115*e* do not interfere with each other. It may be desirable to have a relatively long connecting portion 2115*e*, as the increased length may allow for greater force dampening compared to a smaller connecting portion, all else being equal.

Although the undulating portions of beams 2115 may provide for desirable force dissipation or dampening or absorption, certain potential drawbacks may arise from the use of the undulating portions. For example, while pulling the frame 2100 into a delivery device in preparation for delivery, or while allowing the frame 2100 to deploy from the delivery device during deployment, the undulating portions of the beams 2115 may tend to begin to straighten (e.g., as a result of a tensile force). If the undulating portions of the beams 2115 distorted enough during such straightening, these portions of the frame 2100 might plastically deform, break, or otherwise become damaged, which might jeopardize the proper functioning of the prosthetic heart valve 2010. In order to mitigate this risk, in some embodiments, including that shown in FIG. 10D, the first beam portion 2115*a* may be coupled to the second beam portion 2115*b* via a connecting wire, such as a suture. In one exemplary configuration, a first eyelet 2115*f* may be formed in the frame 2100 in or adjacent the first beam portion 2115*a*, which may face away from the first curved portion 2115*c*, and a second eyelet 2115*g* may be formed in the frame 2100 in or adjacent the second beam portion 2115*b*, which may face away from the second curved portion 2115*d*. These two eyelets 2115*f*, 2115*g* may be coupled via a suture 2115*h* or similar wire-like structure. With this configuration, the suture 2115*h* will help resist the undulating portions of the beams 2115 from straightening, but will not stop the undulating portions of the beams 2115 from compressing to dampen force transferring along the beams 2115. In some embodiments, the sutures 2115*h* may be provided as biodegradable sutures. If the sutures 2115*h* are provided as biodegradable sutures, the sutures will still allow for tension to be applied during loading to the structure without lengthening (or with very little lengthening), but after implantation and tissue ingrowth, the suture 2115*h* might degrade and no longer restrict movement.

Figure 11A:
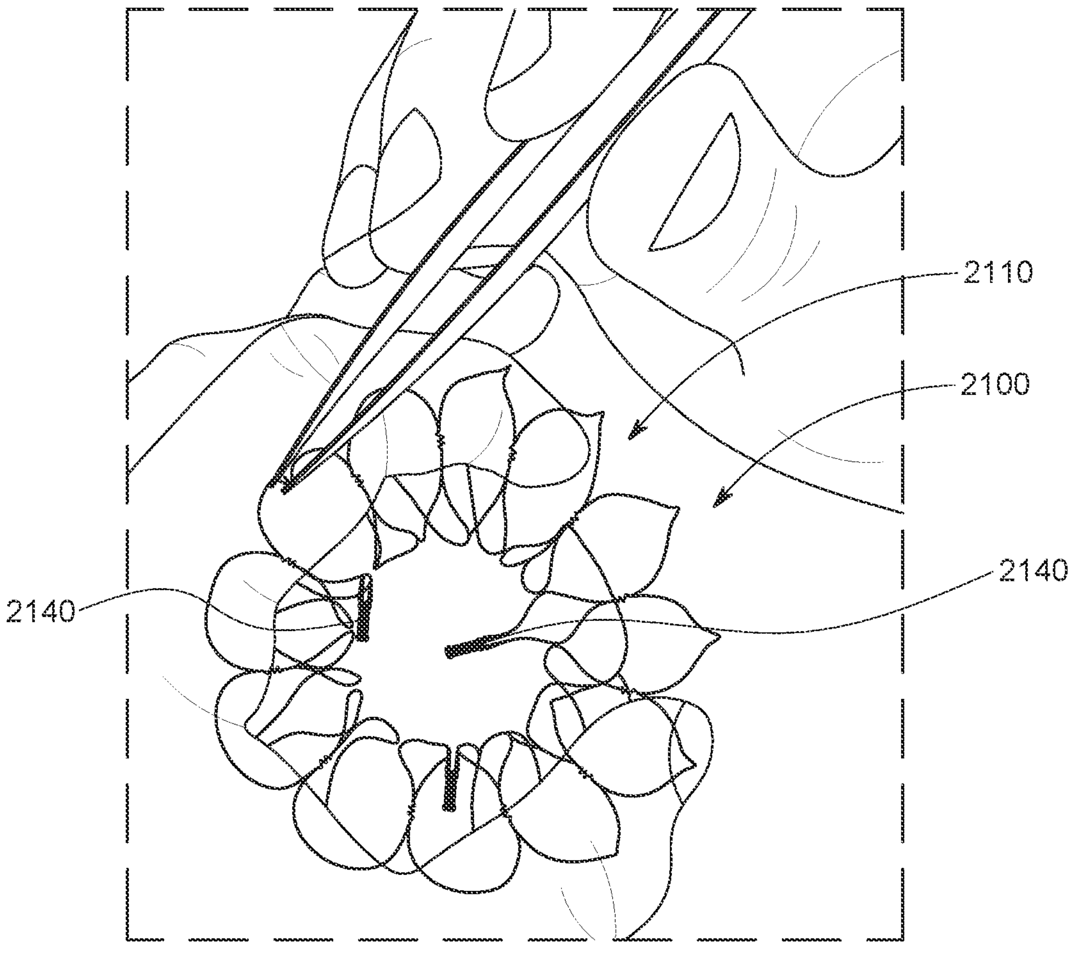
FIGS. 11A-B illustrate the frame of FIG. 10B before and after, respectively, radially inward force is applied to an atrial cell of the frame.
Figure 11B:
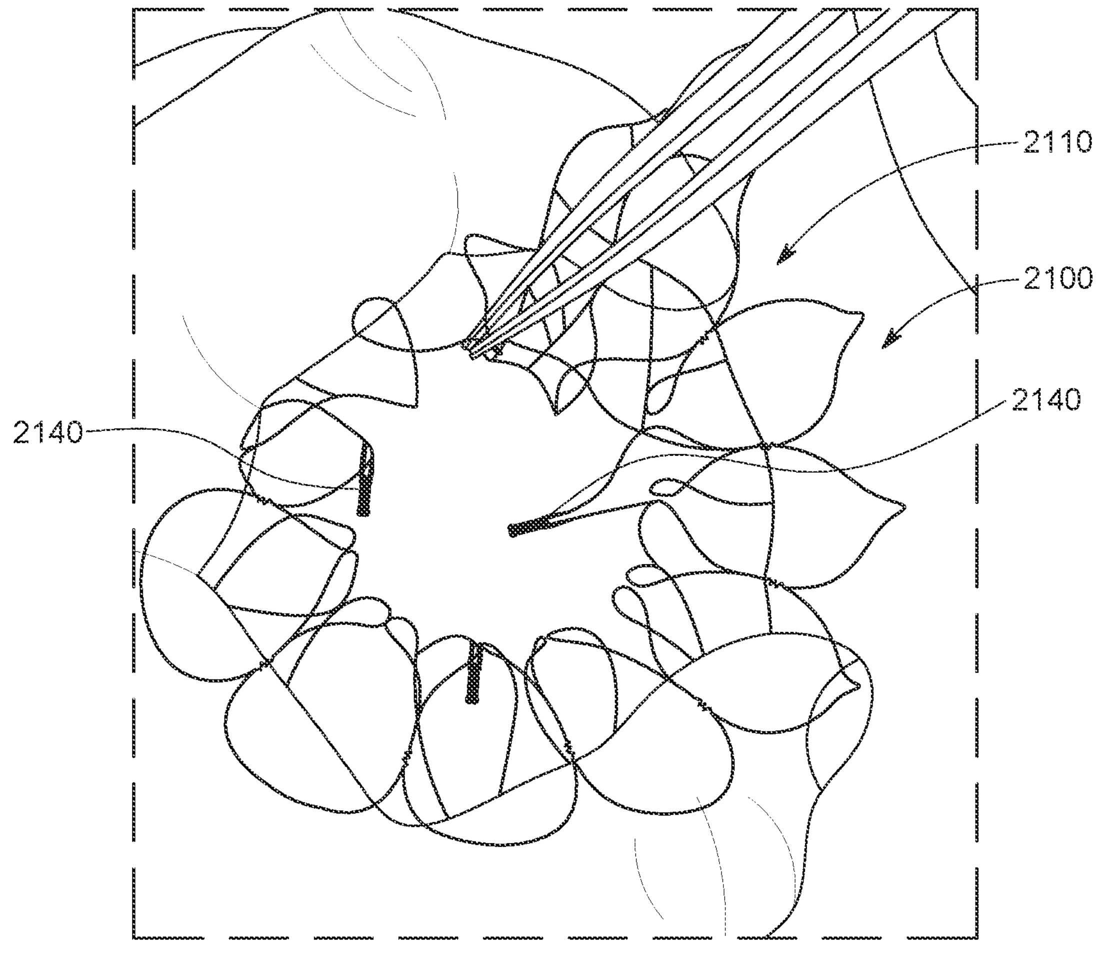

FIGS. 11A-B illustrate one example of the undulating portions of the beams 2115 breaking force applied on the atrial section 2110 from transmitting to the ventricular section 2120. Similar to FIG. 9A, FIG. 11A illustrates forceps or tweezers gripping the atrial tip of an atrial cell 2112 of the atrial portion 2110, without the forceps applying significant force. Similar to FIG. 9B, FIG. 11B illustrates the forceps having pulled the atrial tip of the atrial cell 2112 radially inwardly toward the longitudinal center of the frame 2100. However, unlike FIG. 9B, FIG. 11B shows that the CAF 2140 on the ventricular section 212 of the frame aligned with the atrial cell 2112 being pulled radially inwardly does not change positions (compared to FIG. 11A), despite the significant force being applied to the atrial section 2110 of the frame 2100. In other words, despite motion in the right atrium (represented by the force applied by the forceps), the undulating portion of the beams 2115 allows the frame 2100 to "hinge" about the undulating structure so that the ventricular portion 2120 remains substantially stable while the atrial portion 2110 moves.

In a preferred embodiment, both lateral sides of every atrial cell 2112 include an undulating structure (e.g., at a strut junction where each atrial cell intersects with a circumferentially adjacent atrial cell). However, in other embodiments, fewer undulating structures may be provided. For example, in some embodiments, the undulating structures may be strategically placed, including at positions generally axially aligned with the CAFs 2140. And although the undulating structures are shown as being formed at the side struts of the atrial cells 2112, similar undulating structures could be provided in other locations to provide a similar effect. Preferably, although not necessarily, the number and/or positioning of undulating structures are provided so that force applied to an inflow-most tip of any atrial cell in the atrial portion cannot transmit to an outflow-most tip of any ventricular cell without passing through at least one of the undulating structures.

One of the major benefits of the undulating structures within the beams 2115 is to help to eliminate unwanted deformations in the ventricular portion 2120 of the frame 2100, which may help to eliminate unwanted deformations in the prosthetic leaflets 2500 that are coupled to the CAFs 2140. This may be particularly useful for prosthetic heart valves that are implanted into native anatomy with complex shapes, including atrioventricular annuli that are non-circular or saddle-shaped.

Figure 12A:
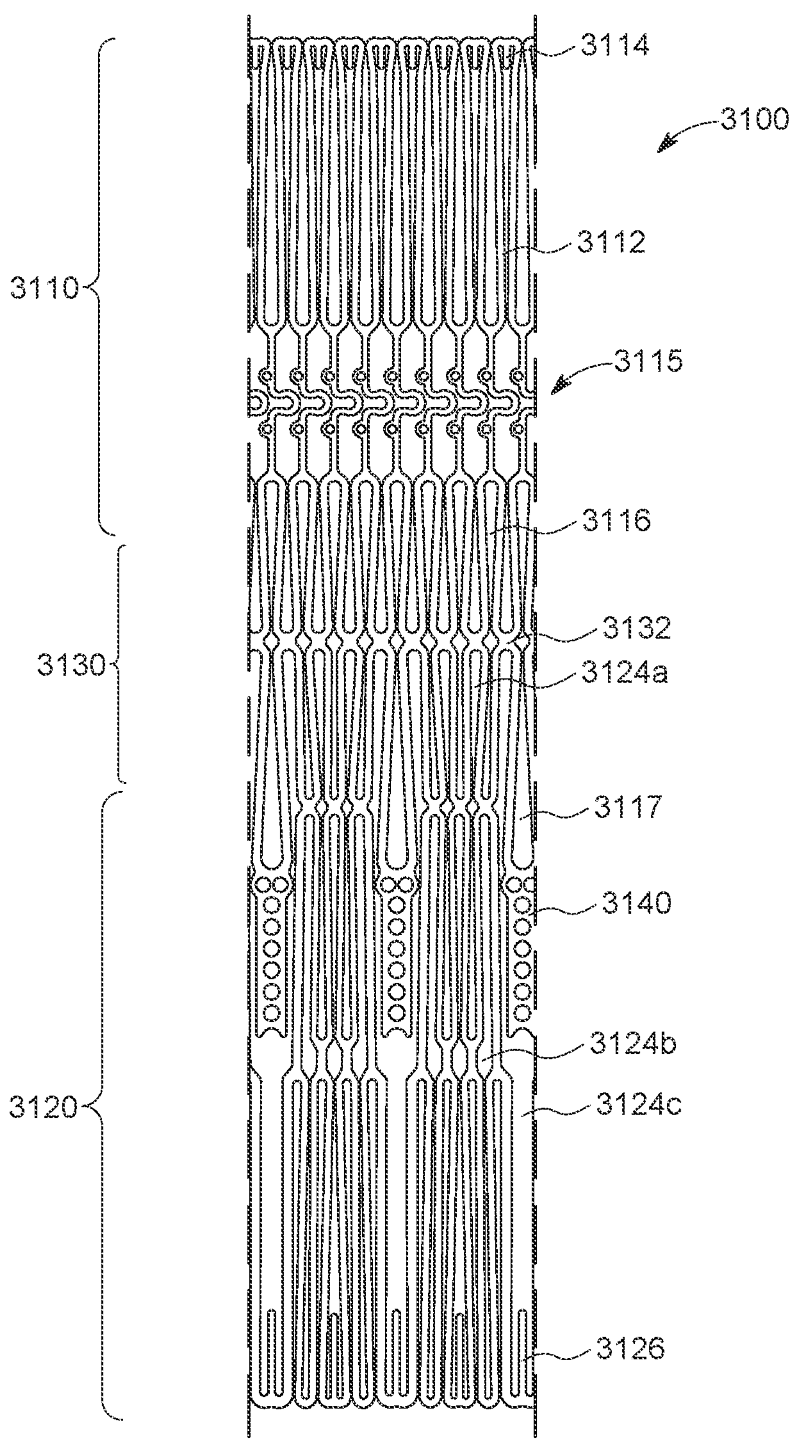
FIG. 12A illustrates a cut pattern similar to that shown in FIG. 10C with an alternative design.
Figure 12B:
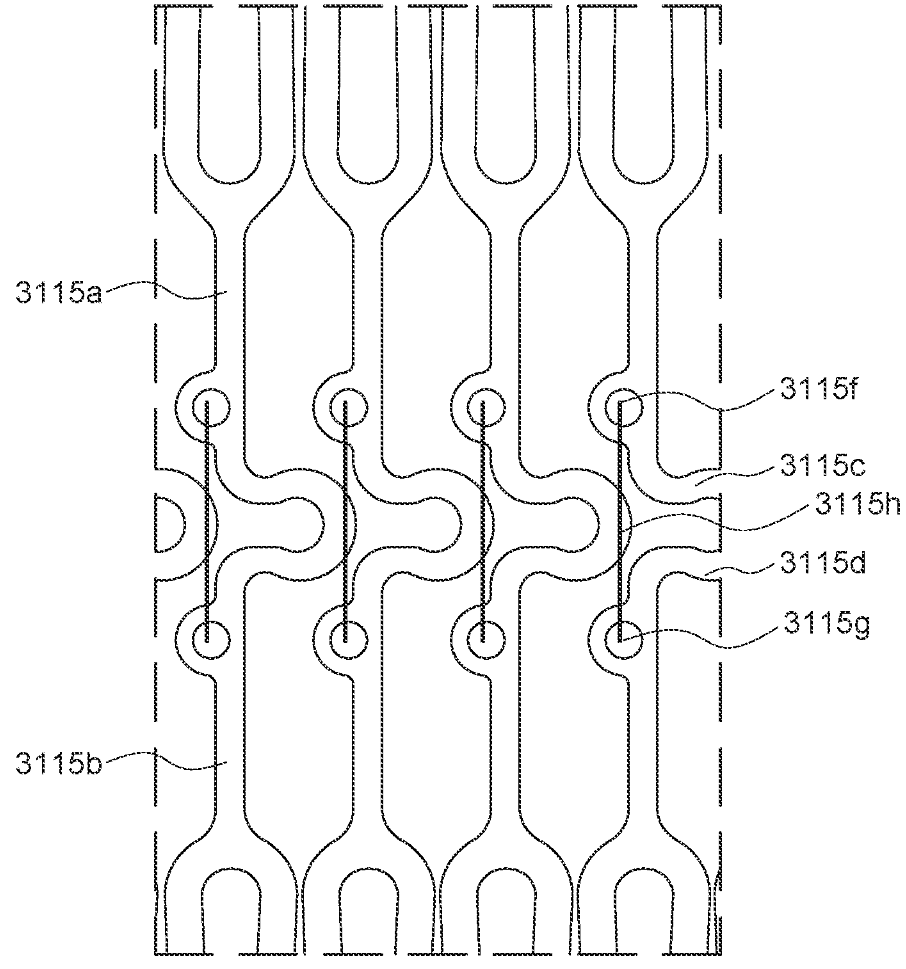
FIG. 12B illustrates a portion of the cut pattern of FIG. 12A.

FIG. 12A illustrates a cut pattern of a frame 3100 that is generally similar to frame 2100, with certain modifications. FIG. 12B illustrates an enlarged view of the beans 3115 of the frame 3100. Due to the similarities between frame 3100 and frame 2100, only the differences of frame 3100 compared to frame 2100 are described below, and thus any feature of frame 3100 not described explicitly may be similar or identical to the corresponding feature of frame 2100 described above.

As with frame 2100, frame 3100 is preferably formed from a shape-memory material, such as a nickel-titanium alloy such as Nitinol, and may be created from a single tube, for example via laser cutting a tube of Nitinol. In the cut patterns shown in FIG. 12A, the frame 3100 generally includes an atrial portion 3110 and a ventricular portion 3120 separated by a center portion 3130. After the frame 3100 is cut and set to the desired shape, for example similar to that shown in FIG. 10B, the center portion 3130 may be very short, particularly in comparison to the center portion 130 of frame 100 shown in FIGS. 1-2.

A plurality of transition cells 3116 may be positioned in a row that is adjacent to the atrial cells 3112 in the outflow direction. The row of transition cells 3116 may include three enlarged transition cells 3117 (or more or fewer than three depending on the number of prosthetic leaflets included in the prosthetic heart valve) that terminate in a commissure attachment feature ("CAF") 3140. Each CAF 3140 may serve as an attachment point to a pair of the prosthetic leaflets. CAFs 3140 may be identical to CAFs 2140, or have an alternate design in which only one end of the "dog-bone" shape is included on the atrial or inflow side of the CAF 3140. In other words, CAFs 3140 may include two eyelets in a top or atrial most row, and a single column of eyelets in the outflow direction, without a corresponding pair of two eyelets in a bottom or ventricular most row.

The portion of the frame 3100 in the outflow direction of the inflection point 3132 may include a plurality of ventricular cells, including a group of first ventricular cells 3124*a*, the inflow apex of which is an inflection point 3132. A group of second ventricular cells 3124*b* may extend to the outflow-most portion of the frame 3100, the inflow apices of the second ventricular cells being connected to the outflow apices of the transition cells 3116. A group of third ventricular cells 3124*c* may be positioned between certain pairs of second ventricular cells 3124*b*, and may include struts that extend from the inflection point 3132 to the terminal outflow end of the ventricular portion 3120. Third ventricular cells 3124*c* may be larger than the other ventricular cells and may be formed in part by the struts of enlarged transition cells 3117 that terminate at CAFs 3140. With this configuration, at least in the cut pattern shown in FIG. 12A, the CAFs 3140 may be thought of as either nested within third ventricular cells 3124*c* or forming a boundary of third ventricular cells 3124*c*.

In the illustrated embodiment, frame 3100 includes tines 3126 extending atrially from the outflow apexes of the third ventricular cells 3124*c* and from the outflow apexes of selected ones of the second ventricular cells 3124*b* (e.g., from the middle one of each group of three consecutive second ventricular cells 3124*b*). Tines 3126 may be substantially similar in structure to tines 1126 and serve the same purpose. As with frame 1100, the tines 3126 may be provided in different numbers, positions, and/or configurations than shown in FIG. 12A, and may otherwise be omitted entirely. The tines 3126 may be shape set in similar ways as described in connection with tines 1126.

Similar to frame 2100, frame 3100 includes longitudinally extending beams 3115 that are interrupted by a contoured or wave-shaped or undulating portion configured to "break" force transmission along the beams 3115 from the atrial portion 3110 to the center portion 3130 and ventricular portion 3120 (and vice versa). It should be understood that the term "undulating" as used herein is not intended to refer to only one specific structural shape. In other words, although the undulating structure shown and described in greater detail below generally has a sinusoidal or wavy or zig-zag type of shape, as used herein, the term "undulating" refers to any structure that (i) has a shape other than a longitudinal beam and (ii) allows for force dampening across the structure.

FIG. 12B illustrates an enlarged view of the beams 3115 of frame 3100. Each beam 3115 may include a first longitudinal beam portion 3115*a* (e.g., toward an inflow-side) and a second longitudinal beam portion 3115*b* (e.g., toward an outflow-side), with the two beam portions 3115*a*, 3115*b* separated by the undulating structure. The two longitudinal beam portions 3115*a*, 3115*b* may be axially aligned with each other. The two longitudinal beam portions 3115*a*, 3115*b* may be separated by an undulating or wave portion, which may be a generally sinusoidal (or partially-sinusoidal) or other undulating shape. For example, in the illustrated embodiment, each beam 3115 may include a first curved portion 3115*c* that curves generally circumferentially in a first direction from the first beam portion 3115*a*, and a second curved portion 3115*d* that curves generally circumferentially in a second direction, opposite the first direction, to connect back to the second beam portion 3115*b*. The two curved portions 3115*c*, 3115*d* may together for ma general "U"-shape or "C"-shape or "Omega"-shape. With the above-described configuration, axial force transmitted along either of the longitudinal beam portions 3115*a*, 3115*b* will tend to cause the various curved portions 3115*c*, 3115*d* to compress, dampening the force transmission so that little or no force is transmitted from one of the beam portions (3115*a* or 3115*b*) to the other of the beam portions (3115*a* or 3115*b*). It should be understood that, after being shape-set, the frame 3100 is not a flat, generally two-dimensional structure. Thus, although the undulating portions of the beams 3115 may generally compress to "break" (or absorb or dampen) force transmission across the length of the beams 3115, the undulation portions may also move in other dimensions to assist with isolating force applied on the atrial portion 3110 from transmitting to the ventricular portion 3120 (and vice versa).

Although the undulating portions of beams 3115 may provide for desirable force dissipation or dampening or absorption, certain potential drawbacks may arise from the use of the undulating portions. For example, while pulling the frame 3100 into a delivery device in preparation for delivery, or while allowing the frame 3100 to deploy from the delivery device during deployment, the undulating portions of the beams 3115 may tend to begin to straighten (e.g., as a result of a tensile force). If the undulating portions of the beams 3115 distorted enough during such straightening, these portions of the frame 3100 might plastically deform, break, or otherwise become damaged, which might jeopardize the proper functioning of the prosthetic heart valve. In order to mitigate this risk, in some embodiments, including that shown in FIG. 12B, the first beam portion 3115*a* may be coupled to the second beam portion 3115*b* via a connecting wire, such as a suture. In one exemplary configuration, a first eyelet 3115*f* may be formed in the frame 3100 in or adjacent the first beam portion 3115*a*, which may face away from the first curved portion 3115*c*, and a second eyelet 3115*g* may be formed in the frame 3100 in or adjacent the second beam portion 3115*b*, which may face away from the second curved portion 3115*d*. These two eyelets 3115*f*, 3115*g* may be coupled via a suture 3115*h* or similar wire-like structure. With this configuration, the suture 3115*h* will help resist the undulating portions of the beams 3115 from straightening, but will not stop the undulating portions of the beams 3115 from compressing to dampen force transferring along the beams 3115. In some embodiments, the sutures 3115*h* may be provided as biodegradable sutures. If the sutures 3115*h* are provided as biodegradable sutures, the sutures will still allow for tension to be applied during loading to the structure without lengthening (or with very little lengthening), but after implantation and tissue ingrowth, the suture 3115*h* might degrade and no longer restrict movement.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve for replacing a native atrioventricular valve, the prosthetic heart valve comprising:

a collapsible and expandable frame, the frame including an atrial portion including a circumferential row of cells, a ventricular portion including a circumferential row of cells, and a center portion extending between the atrial portion and the ventricular portion, the atrial portion and the ventricular portion flaring radially outwardly from the center portion in an expanded condition of the frame; and a plurality of prosthetic leaflets mounted to the frame;

wherein at least some of the struts forming the cells in the atrial portion include an undulating structure positioned and connected between two axially extending strut portions, the axially extending strut portions including a first inflow-side axially extending strut portion and a second outflow-side axially extending strut portion, the first inflow-side axially extending strut portion including a first eyelet formed therein and the second outflow-side axially extending strut portion including a second eyelet formed therein, the undulating structure including at least one circumferentially extending strut portion and being configured to dampen forces transmitted across the undulating structure between the two axially extending strut portions.

2. The prosthetic heart valve of claim 1, wherein the frame includes a number of undulating structures so that force applied to an inflow-most tip of any atrial cell in the atrial portion cannot transmit to an outflow-most tip of any ventricular cell without passing through at least one of the undulating structures.

3. The prosthetic heart valve of claim 2, wherein each of the atrial cells intersects with a circumferentially adjacent atrial cell at a strut junction, and each of the strut junctions includes one of the undulating structures.

4. The prosthetic heart valve of claim 1, wherein the undulating structure includes a first curved portion extending from the first inflow-side axially extending strut portions, and a second curved portion extending from the second outflow-side axially extending strut portion.

5. The prosthetic heart valve of claim 4, wherein the at least one circumferentially extending strut portion couples the first curved portion to the second curved portion.

6. The prosthetic heart valve of claim 4, wherein the first curved portion extends in a first circumferential direction, and the second curved portion extends in a second circumferential direction opposite the first circumferential direction.

7. The prosthetic heart valve of claim 1, further comprising a suture member passing into the first eyelet and the second eyelet so that the suture member couples the first inflow-side axially extending strut portion to the second outflow-side axially extending strut portion.

8. The prosthetic heart valve of claim 7, wherein the suture member limits movement of the second outflow-side axially extending strut portion away from the first inflow-side axially extending strut portion to prevent the undulating structure from straightening upon application of a tensile force.

9. The prosthetic heart valve of claim 8, wherein the suture member enables movement of the second outflow-side axially extending strut portion axially toward the first inflow-side axially extending strut portion to allow the undulating structure to compress upon application of a compressive force.

10. The prosthetic heart valve of claim 1, wherein each circumferentially extending strut portion has a length that is greater than a distance between circumferentially adjacent pairs of the first inflow-side axially extending strut portions.

11. The prosthetic heart valve of claim 10, wherein each circumferentially extending strut portion is offset, in an axial direction, from circumferentially adjacent pairs of circumferentially extending strut portions.

12. The prosthetic heart valve of claim 11, wherein each of the first inflow-side axially extending strut portions has an axial length that is different from the axial length of circumferentially adjacent pairs of the first inflow-side axially extending strut portions.

13. The prosthetic heart valve of claim 1, further comprising a sealing skirt positioned on an exterior surface of the frame.

14. The prosthetic heart valve of claim 1, wherein the frame includes a plurality of commissure attachment features ("CAFs"), each of the prosthetic leaflets being coupled to the frame via the CAFs.

15. The prosthetic heart valve of claim 14, wherein each CAF is an axially extending beam including a single column of eyelets.

16. The prosthetic heart valve of claim 15, wherein each CAF includes a pair of circumferentially adjacent eyelets adjacent to each end of the single column of eyelets.

17. The prosthetic heart valve of claim 14, wherein each CAF is coupled to struts that extend to the center portion of the frame, so that in the expanded condition of the frame, the CAFs are generally axially aligned with the center portion of the frame and the center portion of the frame defines a minimum diameter of the frame.

18. The prosthetic heart valve of claim 1, wherein the frame includes a plurality of tines on the ventricular portion, each of the plurality of tines extending to a free end pointing toward the atrial portion in a collapsed condition of the frame.

* * * * *